(12) United States Patent
Li et al.

(10) Patent No.: US 11,220,501 B2
(45) Date of Patent: Jan. 11, 2022

(54) SOLID FORMS OF {6-[(2-AMINO-3-CHLOROPYRIDIN-4-YL) SULFANYL]-3-[(3S,4S)-4-AMINO-3-METHYL-2-OXA-8- AZASPIRO[4.5]DECAN-8-YL]-5-METHYLPYRAZIN-2-YL} METHANOL, A SHP2 INHIBITOR

(71) Applicant: Revolution Medicines, Inc., Redwood City, CA (US)

(72) Inventors: Shaoling Li, Redwood City, CA (US); Steven G. Ballmer, Redwood City, CA (US)

(73) Assignee: Revolution Medicines, Inc., Redwood City, CA (US)

( * ) Notice: Subject to any disclaimer, the term of this patent is extended or adjusted under 35 U.S.C. 154(b) by 0 days.

(21) Appl. No.: 17/187,504

(22) Filed: Feb. 26, 2021

(65) Prior Publication Data

US 2021/0253574 A1    Aug. 19, 2021

Related U.S. Application Data

(63) Continuation of application No. PCT/US2020/036137, filed on Jun. 4, 2020.

(60) Provisional application No. 62/858,837, filed on Jun. 7, 2019.

(51) Int. Cl.
C07D 471/10    (2006.01)

(52) U.S. Cl.
CPC ........ *C07D 471/10* (2013.01); *C07B 2200/13* (2013.01)

(58) Field of Classification Search
None
See application file for complete search history.

(56) References Cited

U.S. PATENT DOCUMENTS

2020/0368238 A1    11/2020    Nichols et al.

FOREIGN PATENT DOCUMENTS

| WO | WO 2018/013597 A1 | 1/2018 |
| WO | WO 2019/051084 A1 | 3/2019 |
| WO | WO 2019/199792 A1 | 10/2019 |
| WO | WO 2020/247643 A1 | 12/2020 |

OTHER PUBLICATIONS

International Search Report dated Sep. 18, 2020, for International Applicational No. PCT/US2020/036137, 3 pages.

*Primary Examiner* — Heidi Reese
(74) *Attorney, Agent, or Firm* — McNeill Baur PLLC

(57) ABSTRACT

The present disclosure relates to crystalline solid forms of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, the process of preparing the forms, and pharmaceutical compositions and methods of use thereof.

33 Claims, 14 Drawing Sheets

SOLID FORMS OF {6-[(2-AMINO-3-CHLOROPYRIDIN-4-YL) SULFANYL]-3-[(3S,4S)-4-AMINO-3-METHYL-2-OXA-8- AZASPIRO[4.5]DECAN-8-YL]-5-METHYLPYRAZIN-2-YL} METHANOL, A SHP2 INHIBITOR

CROSS REFERENCE TO RELATED APPLICATIONS

This application is a continuation of International Application No. PCT/US2020/036137, filed Jun. 4, 2020, which claims the benefit of U.S. Provisional Application No. 62/858,837, filed Jun. 7, 2019, the contents of each of which are incorporated herein by reference in their entirety.

FIELD OF DISCLOSURE

The present disclosure relates to crystalline solid forms of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, also called 6-((2-amino-3-chloropyridin-4-yl)thio)-3-((3S,4S)-4-amino-3-methyl-2-oxa-8-azaspiro[4.5]decan-8-yl)-5-methylpyrazin-2-yl)methanol, or a pharmaceutically acceptable salt thereof, the process of preparing the forms, and pharmaceutical compositions and methods of use thereof.

Background of the Disclosure

Src homology region 2-containing protein tyrosine phosphatase (SHP2) is a non-receptor protein tyrosine phosphatase encoded by the PTPNI1 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N-SH2 and C-SH2), a catalytic domain (PTP), and a C-terminal tail. The two SH2 domains control the subcellular localization and functional regulation of SHP2. The protein exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

Mutations in the PTPNI1 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present disclosure fulfill the need for small molecules to that inhibit the activity of SHP2.

SUMMARY OF THE DISCLOSURE

The present disclosure relates to crystalline solid forms of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, the process of preparing the forms, and pharmaceutical compositions and methods of use thereof.

The present disclosure provides a crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form D.

The present disclosure provides a crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form B.

The present disclosure provides a crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form C.

The present disclosure provides a crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form A.

Another aspect of the disclosure is directed to pharmaceutical compositions comprising one or more compounds disclosed herein (e.g., Compound 1 Form A, Compound 1 Form B, Compound 1 Form C, or Compound 1 Form D, and pharmaceutically acceptable salts thereof), and a pharmaceutically acceptable carrier. The pharmaceutically acceptable carrier can further comprise an excipient, diluent, or surfactant. The pharmaceutical composition can be effective for treating a disease associated with SHP2 modulation in a subject in need thereof.

Another aspect of the disclosure relates to methods of treating a disease associated with SHP2 modulation in a subject in need thereof, comprising administering to the subject an effective amount of one or more compounds disclosed herein (e.g., Compound 1 Form A, Compound 1 Form B, Compound 1 Form C, or Compound 1 Form D, and pharmaceutically acceptable salts thereof).

Another aspect of the disclosure relates to methods of inhibiting SHP2. The method comprises administering to a patient in need thereof, an effective amount of one or more compounds disclosed herein (e.g., Compound 1 Form A, Compound 1 Form B, Compound 1 Form C, or Compound 1 Form D, and pharmaceutically acceptable salts thereof).

Another aspect of the disclosure relates to methods of treating a disease associated with SHP2 modulation in a subject in need thereof, comprising administering to the subject an effective amount of a pharmaceutical composition comprising one or more compounds disclosed herein (e.g., Compound 1 Form A, Compound 1 Form B, Compound 1 Form C, or Compound 1 Form D, and pharmaceutically acceptable salts thereof).

Another aspect of the disclosure relates to methods of inhibiting SHP2 comprising administering to a patient in need thereof, an effective amount of a pharmaceutical composition comprising one or more compounds disclosed herein (e.g., Compound 1 Form A, Compound 1 Form B, Compound 1 Form C, or Compound 1 Form D, and pharmaceutically acceptable salts thereof).

Another aspect of the disclosure relates to one or more compounds disclosed herein (e.g., Compound 1 Form A, Compound 1 Form B, Compound 1 Form C, or Compound 1 Form D, and pharmaceutically acceptable salts thereof), for use in treating or preventing a disease associated with SHP2 modulation. One aspect of the disclosure relates to pharmaceutical compositions comprising one or more compounds disclosed herein (e.g., Compound 1 Form A, Compound 1 Form B, Compound 1 Form C, or Compound 1 Form D, and pharmaceutically acceptable salts thereof), and a pharmaceutically acceptable carrier, for use in treating of preventing a disease associated with SHP2 modulation.

Another aspect of the disclosure relates to the use of one or more compounds disclosed herein (e.g., Compound 1 Form A, Compound 1 Form B, Compound 1 Form C, or Compound 1 Form D, and pharmaceutically acceptable salts thereof), in the manufacture of a medicament for treating or preventing a disease associated with SHP2 modulation. Another aspect of the disclosure relates to the use of pharmaceutical compositions comprising one or more compounds disclosed herein (e.g., Compound 1 Form A, Compound 1 Form B, Compound 1 Form C, or Compound 1 Form D, and pharmaceutically acceptable salts thereof), and a pharmaceutically acceptable carrier, in the manufacture of a medicament for treating or preventing a disease associated with SHP2 modulation.

Another aspect of the disclosure relates to one or more compounds disclosed herein (e.g., Compound 1 Form A, Compound 1 Form B, Compound 1 Form C, or Compound 1 Form D, and pharmaceutically acceptable salts thereof), for use as a medicament. Another aspect of the disclosure relates to pharmaceutical compositions comprising one or more compounds disclosed herein (e.g., Compound 1 Form A, Compound 1 Form B, Compound 1 Form C, or Compound 1 Form D, and pharmaceutically acceptable salts thereof), for use as a medicament. In some embodiments, the medicament is used for treating or preventing a disease associated with SHP2 modulation.

The present disclosure also provides compounds and pharmaceutical compositions that are useful in inhibiting SHP2.

DETAILED DESCRIPTION OF THE DISCLOSURE

Figure 1A:
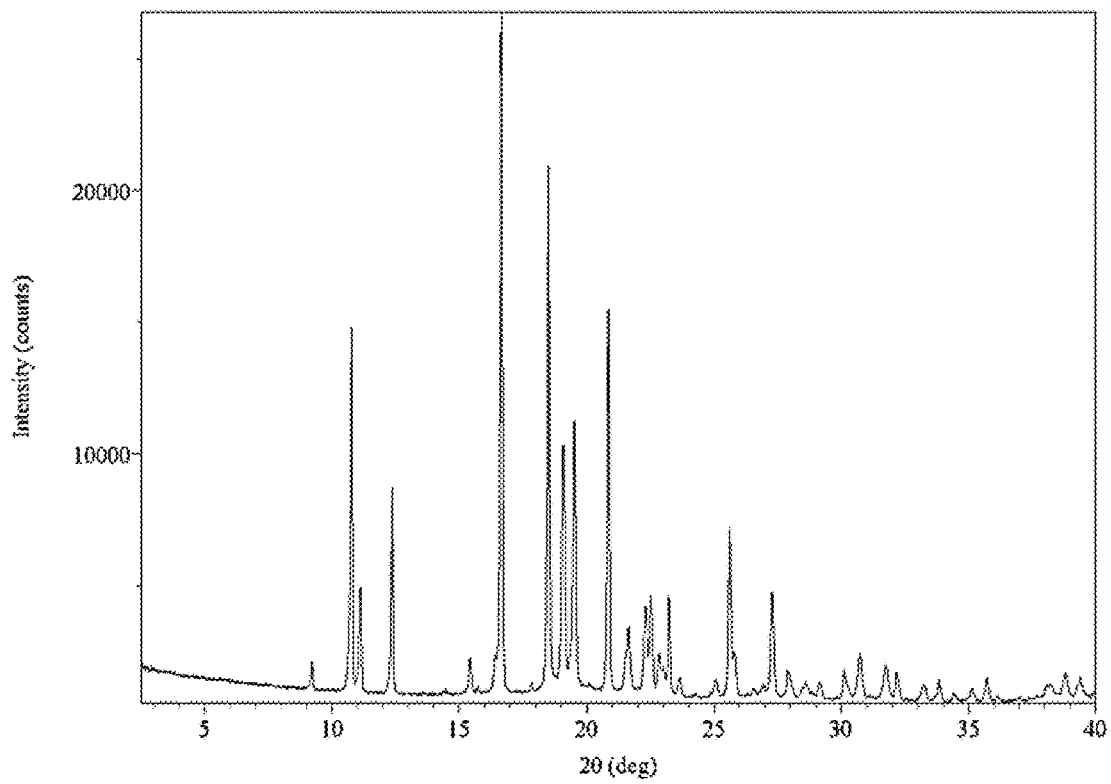
FIG. 1A is an X-ray diffraction pattern of Compound 1 Form A.

The present disclosure provides crystalline solid forms of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, also called 6-((2-amino-3-chloropyridin-4-yl)thio)-3-((3S,4S)-4-amino-3-methyl-2-oxa-8-azaspiro[4.5]decan-8-yl)-5-methylpyrazin-2-yl)methanol, (Compound 1). The present disclosure also provides pharmaceutical compositions comprising crystalline solid forms of Compound 1. The disclosure also provides processes for making the crystalline solid forms and methods for using them.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Each embodiment described herein may be taken alone or in combination with any one or more other embodiments.

Terms

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

An "effective amount" when used in connection with a compound is an amount effective for treating or preventing a disease in a subject as described herein.

The term "carrier," as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "prevent" or "preventing" with regard to a subject refers to keeping a disease or disorder from afflicting the subject. Preventing includes prophylactic treatment. For instance, preventing can include administering to the subject one or more compounds disclosed herein before a subject is afflicted with a disease and the administration will keep the subject from being afflicted with the disease.

The term "disorder" is used in this disclosure to mean, and is used interchangeably with, the terms disease, condition, or illness, unless otherwise indicated.

The term "administer," "administering," or "administration" as used in this disclosure refers to either directly administering one or more disclosed compounds or a pharmaceutically acceptable salt of one or more disclosed compounds or a composition comprising one or more disclosed compounds to a subject, or administering a prodrug derivative or analog of the compound or a pharmaceutically acceptable salt of the compound or composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

An "XRPD pattern" is an x-y graph with diffraction angle (i.e., °2θ) on the x-axis and intensity on the y-axis. The peaks within this pattern may be used to characterize a crystalline solid form. As with any data measurement, there is variability in XRPD data. The data are often represented solely by the diffraction angle of the peaks rather than including the intensity of the peaks because peak intensity can be particularly sensitive to sample preparation (for example, particle size, moisture content, solvent content, and preferred orientation effects influence the sensitivity), so samples of the same material prepared under different conditions may yield slightly different patterns; this variability is usually greater than the variability in diffraction angles. Diffraction angle variability may also be sensitive to sample preparation. Other sources of variability come from instrument parameters and processing of the raw X-ray data: different X-ray instruments operate using different parameters and these may lead to slightly different XRPD patterns from the same solid form, and similarly different software packages process X-ray data differently and this also leads to variability. These and other sources of variability are known to those of ordinary skill in the pharmaceutical arts. Due to such sources of variability, it is usual to assign a variability of about ±0.2°2θ to diffraction angles in XRPD patterns.

Solid Forms

Forms A, B, C, and D are anhydrous polymorphs of Compound 1. Thermal techniques provide data that the relative stability of the forms change with temperature. Both Forms A and C are enantiotropically related to each other and to Form D; Form A is thermodynamically stable above approximately 80° C., Form C is the stable form between approximately 80 and 43° C., and Form D is physically stable below approximately 43° C. Conversion between Forms A, C, and D is immediate (and reversible) upon reaching the corresponding relevant temperatures. Form B appears monotropically related to Form A. Consequently, because of the relationships of Form A relative to Forms C and D (enantiotropic) and Form B (monotropic), Form B is constrained as a metastable form at all temperatures. Tables 1 and 2 show the relationships between the forms and temperature.

TABLE 1

Estimated Transition Point Temperature between Enantiotropic Polymorphs

|  | Form D | Form C | Form B |
|---|---|---|---|
| Form A to | ~65° C. | ~80° C. | monotropic |
| Form B to | undecided | undecided |  |
| Form C to | ~43° C. |  |  |

TABLE 2

Relative Thermodynamic Stability of Polymorphs between each Estimated Transition

| Temperature Range | Relative Stability |
|---|---|
| subambient up to ~43° C. | D > C > A > B |
| between ~43 and ~65° C. | C > D > A > B |
| between ~65 and ~80° C. | C > A > (D and B) |
| above ~80° C. | A > (C and D and B) |

Form A

The present disclosure provides a crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form A.

Compound 1 Form A is a high temperature, anhydrous form that is thermodynamically stable above approximately 80° C. and exhibits a melt near 213° C. (onset temperature measured by differential scanning calorimetry). The tentative unit cell parameters and calculated volume of Form A at ambient temperature, derived from indexing, are: a=14.310 Å, b=15.892 Å, c=9.586 Å, α=90°, β=90°, γ=90°, V=2180.0 Å$^3$. The space group was determined to be P2$_1$2$_1$2.

In general, Compound 1 Form A is generated through spontaneous polymorphic conversion from either Forms C or D (or mixtures thereof) when exposed to temperatures above 80° C. Compound 1 Form A is generated from Form B (or mixtures of Form B with Forms C and/or D) when exposed to temperatures above the melt of Form B (~188° C.) but below the melt of Form A (~213° C.) and allowed to spontaneously crystallize. In certain embodiments, Compound 1 Form A has an onset melting temperature of about 213° C.

In certain embodiments, Compound 1 Form A exhibits an XRPD pattern comprising peaks shown in Table 3 below. Table 4 shows representative peaks for XRPD pattern of Compound 1 Form A.

TABLE 3

Observed Peaks for XRPD Pattern of Compound 1 Form A

| 2θ (°) | d-spacing (Å) | Intensity (%) |
|---|---|---|
| 9.21 ± 0.20 | 9.590 ± 0.208 | 8 |
| 10.76 ± 0.20 | 8.213 ± 0.152 | 56 |
| 11.11 ± 0.20 | 7.960 ± 0.143 | 18 |
| 12.35 ± 0.20 | 7.160 ± 0.115 | 33 |
| 14.47 ± 0.20 | 6.117 ± 0.084 | 4 |
| 15.43 ± 0.20 | 5.738 ± 0.074 | 8 |
| 15.76 ± 0.20 | 5.620 ± 0.071 | 4 |
| 16.43 ± 0.20 | 5.391 ± 0.065 | 9 |
| 16.66 ± 0.20 | 5.317 ± 0.063 | 100 |
| 17.85 ± 0.20 | 4.966 ± 0.055 | 5 |
| 18.50 ± 0.20 | 4.792 ± 0.051 | 79 |
| 19.08 ± 0.20 | 4.648 ± 0.048 | 39 |

TABLE 3-continued

Observed Peaks for XRPD Pattern of Compound 1 Form A

| 2θ (°) | d-spacing (Å) | Intensity (%) |
|---|---|---|
| 19.52 ± 0.20 | 4.545 ± 0.046 | 42 |
| 20.12 ± 0.20 | 4.410 ± 0.043 | 5 |
| 20.85 ± 0.20 | 4.257 ± 0.040 | 58 |
| 21.64 ± 0.20 | 4.104 ± 0.037 | 13 |
| 22.30 ± 0.20 | 3.983 ± 0.035 | 16 |
| 22.52 ± 0.20 | 3.945 ± 0.035 | 17 |
| 22.84 ± 0.20 | 3.890 ± 0.034 | 9 |
| 23.02 ± 0.20 | 3.860 ± 0.033 | 7 |
| 23.22 ± 0.20 | 3.828 ± 0.033 | 17 |
| 23.64 ± 0.20 | 3.760 ± 0.031 | 6 |
| 24.24 ± 0.20 | 3.669 ± 0.030 | 3 |
| 25.06 ± 0.20 | 3.550 ± 0.028 | 5 |
| 25.63 ± 0.20 | 3.472 ± 0.027 | 27 |
| 25.81 ± 0.20 | 3.449 ± 0.026 | 9 |
| 26.57 ± 0.20 | 3.352 ± 0.025 | 4 |
| 26.94 ± 0.20 | 3.307 ± 0.024 | 5 |
| 27.30 ± 0.20 | 3.264 ± 0.023 | 18 |
| 27.93 ± 0.20 | 3.192 ± 0.022 | 6 |
| 28.62 ± 0.20 | 3.117 ± 0.021 | 5 |
| 29.16 ± 0.20 | 3.060 ± 0.021 | 5 |

TABLE 4

Representative Peaks for XRPD Pattern of Compound 1 Form A

| 2θ (°) | d-spacing (Å) | Intensity (%) |
|---|---|---|
| 10.76 ± 0.20 | 8.213 ± 0.152 | 56 |
| 11.11 ± 0.20 | 7.960 ± 0.143 | 18 |
| 12.35 ± 0.20 | 7.160 ± 0.115 | 33 |
| 16.66 ± 0.20 | 5.317 ± 0.063 | 100 |
| 18.50 ± 0.20 | 4.792 ± 0.051 | 79 |
| 19.08 ± 0.20 | 4.648 ± 0.048 | 39 |
| 19.52 ± 0.20 | 4.545 ± 0.046 | 42 |
| 20.85 ± 0.20 | 4.257 ± 0.040 | 58 |
| 25.63 ± 0.20 | 3.472 ± 0.027 | 27 |

In certain embodiments, Compound 1 Form A is characterized by one or more peaks at about 16.50 to about 16.90 degrees and about 18.30 to about 18.70 degrees in X-ray powder diffraction. In certain embodiments, Compound 1 Form A is characterized by one or more peaks at about 10.50 to about 10.90 degrees, about 10.90 to about 11.30 degrees, about 12.10 to about 12.50 degrees, about 16.50 to about 16.90 degrees, about 18.30 to about 18.70 degrees, about 18.80 to about 19.20 degrees, about 19.30 to about 19.70 degrees, about 20.60 to about 21.00 degrees, and about 25.40 to about 25.80 degrees in X-ray powder diffraction.

In certain embodiments, Compound 1 Form A is characterized by its X-ray powder diffractogram that comprises peaks at about 16.66 and about 18.50020. In certain embodiments, the diffractogram further comprises one or more additional peaks selected from the following peaks at about 10.76, about 11.11, about 12.35, about 19.08, about 19.52, about 20.85, and about 25.63°2θ. Compound 1 Form A is also characterized by its X-ray powder diffractogram as substantially shown in FIG. 1A or FIG. 1B.

Form B

The present disclosure provides a crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form B.

Figure 2:
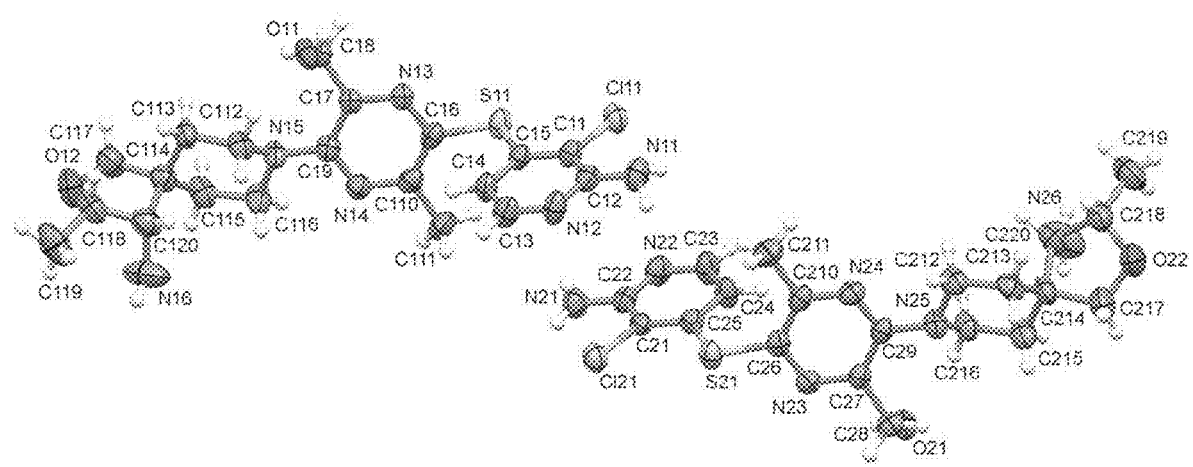
FIG. 2 is atomic ellipsoid diagram for Compound 1 Form B from a single crystal structure.
Figure 3A:
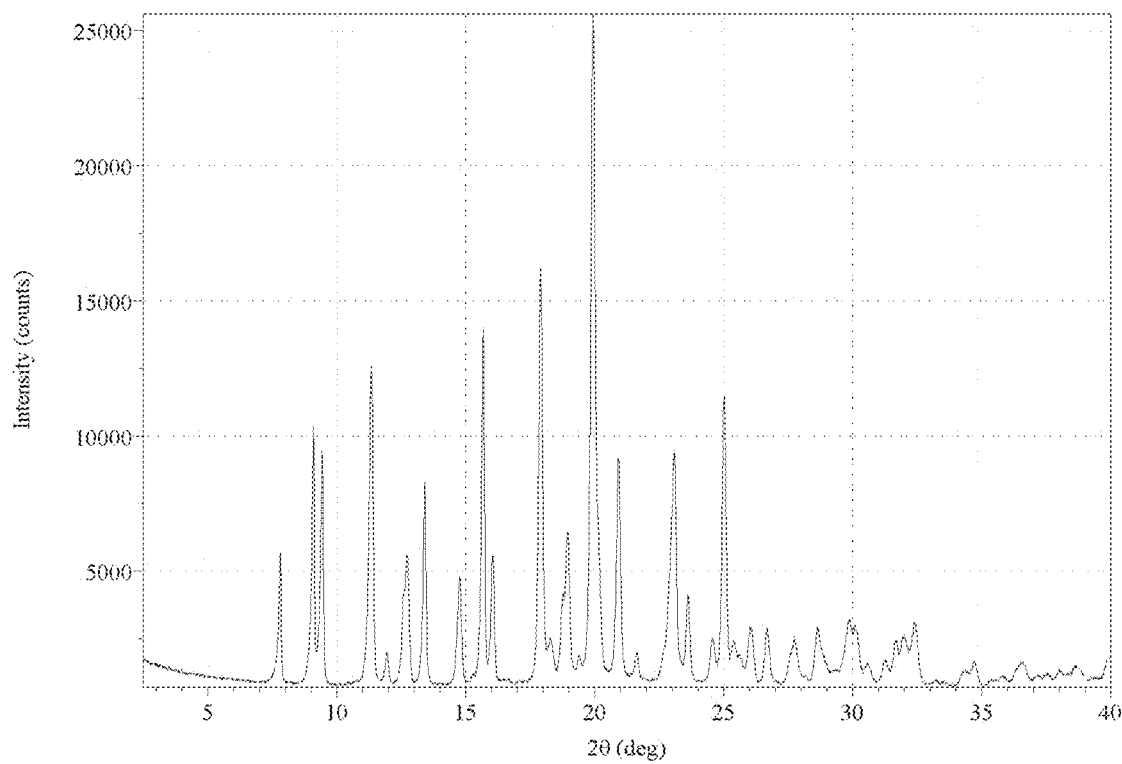
FIG. 3A is an X-ray diffraction pattern of Compound 1 Form B with intensity up to about 25000 counts.
Figure 3B:
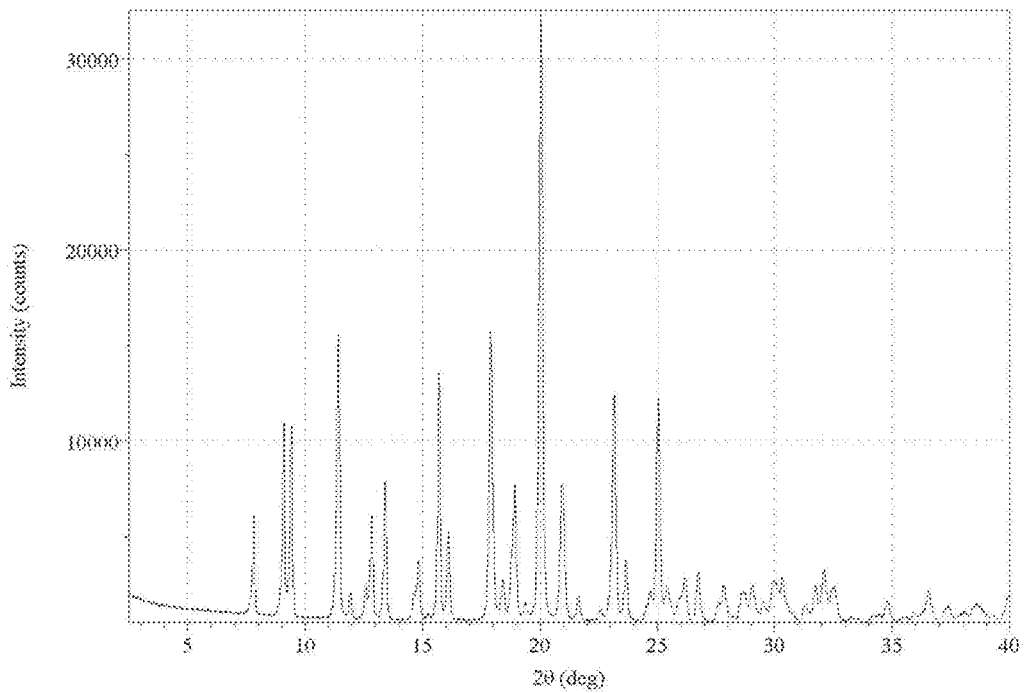
FIG. 3B is an X-ray diffraction pattern of Compound 1 Form B with intensity up to about 30000 counts.
Figure 3C:
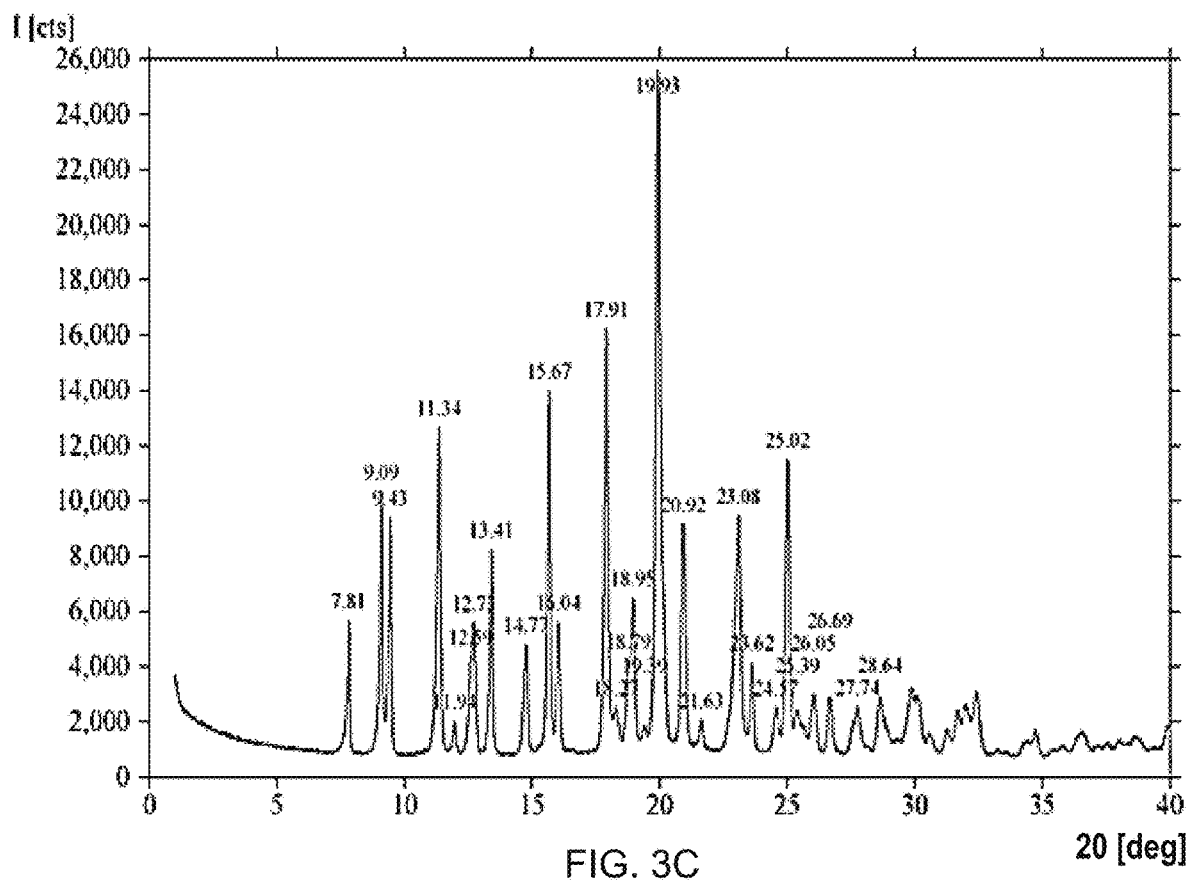
FIG. 3C is an X-ray diffraction pattern of Compound 1 Form B with intensity up to about 26000 counts with observed peaks.
Figure 3D:
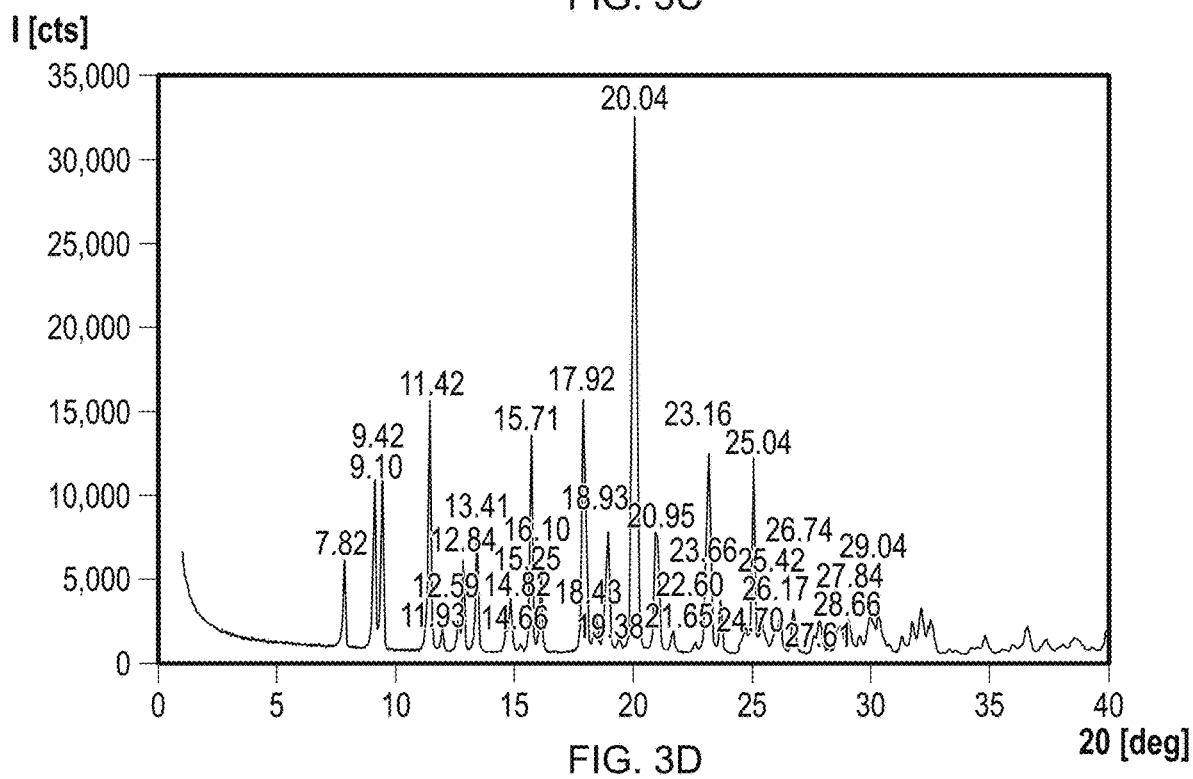
FIG. 3D is an X-ray diffraction pattern of Compound 1 Form B with intensity up to about 35000 counts with observed peaks.

Form B is an anhydrous, metastable form with a likely melt near 188° C. (onset temperature measured by differential scanning calorimetry). The unit cell parameters and calculated volume of Form B, derived from the single crystal structure, are: a=9.65334(16) Å, b=10.28825(18) Å, c=11.62614(19) Å, α=76.0621(15)°, β=89.6714(13)°, γ=76.4043(15)°, V=1087.68(3) Å$^3$. The space group was determined to be P1. The asymmetric unit contains two Compound 1 molecules. The absolute configuration was determined conclusively and Compound 1 was found to bond in the S and S configuration at C120 (C220) and C118 (C218), respectively. FIG. 2 shows an atomic displacement ellipsoid diagram for Compound 1 Form B from single crystal structure.

The differential scanning calorimetry thermogram of Compound 1 Form B exhibits two endotherms with onsets near 188 and 211° C. The endotherm near 188° C. is likely the melt of Form B, which is immediately followed by recrystallization to Compound 1 Form A and the melting of Compound 1 Form A.

Figure 4:
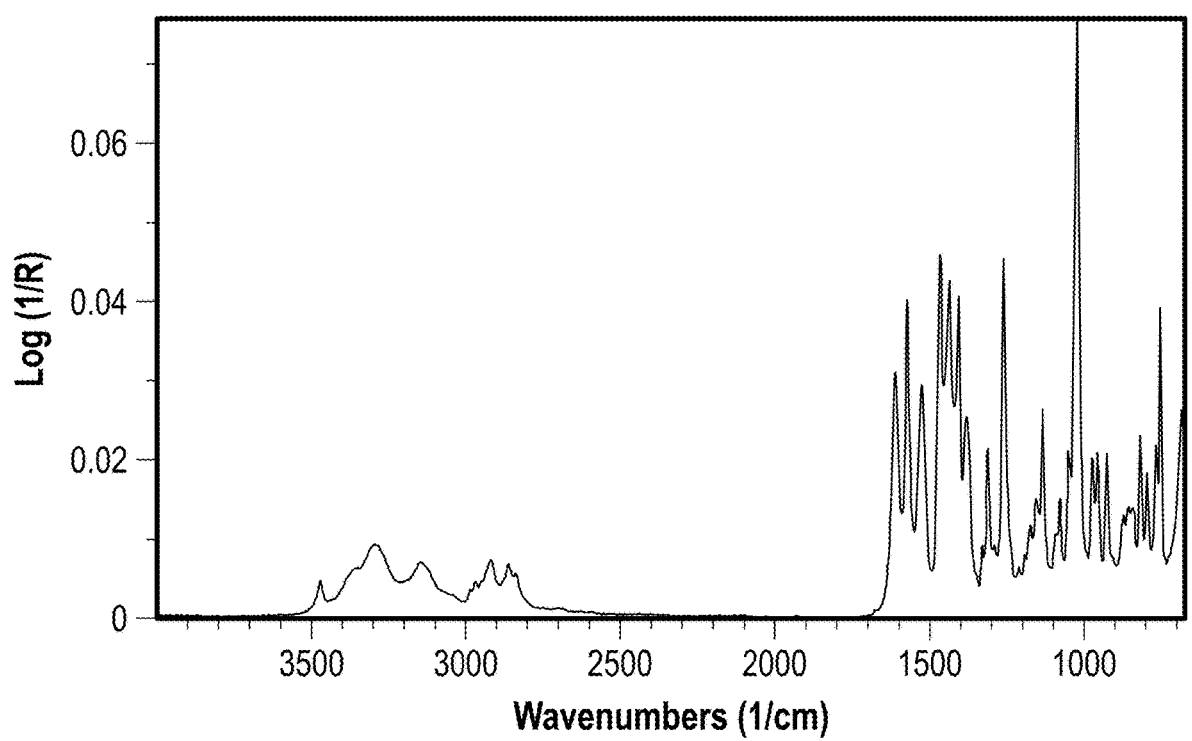
FIG. 4 is an infrared spectrum of Compound 1 Form B.
Figure 5A:
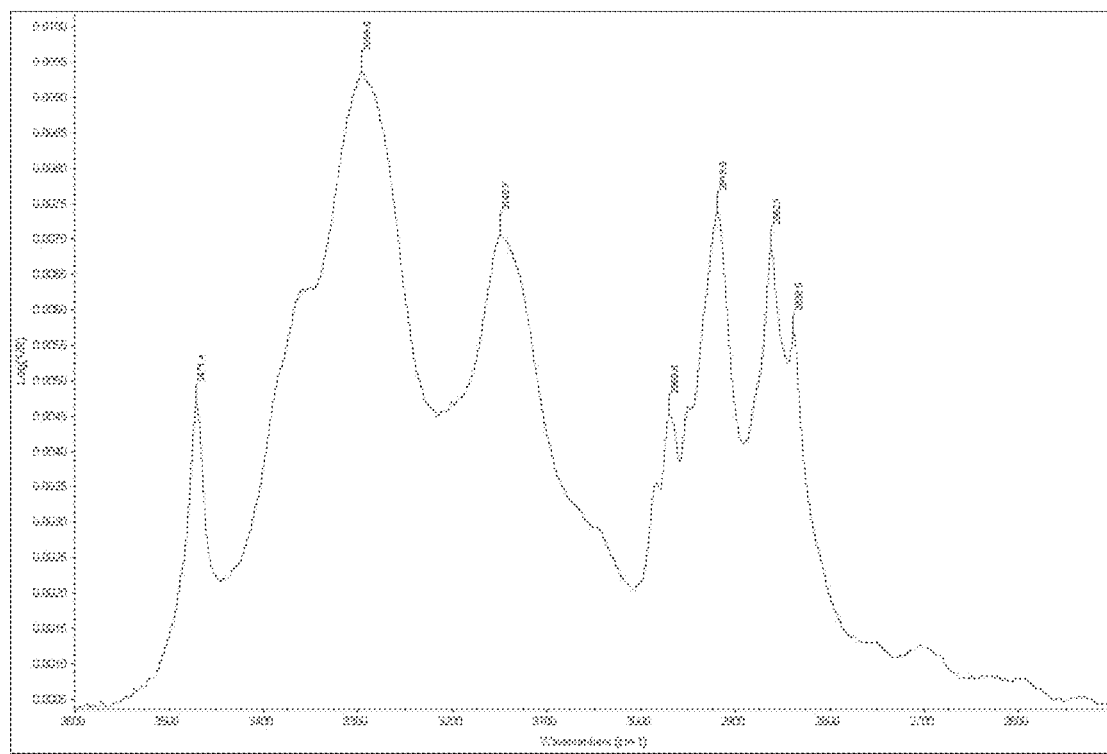
FIG. 5A is an infrared spectrum of Compound 1 Form B with spectral region of about 3600 to 2500 $cm^{-1}$.
Figure 5B:
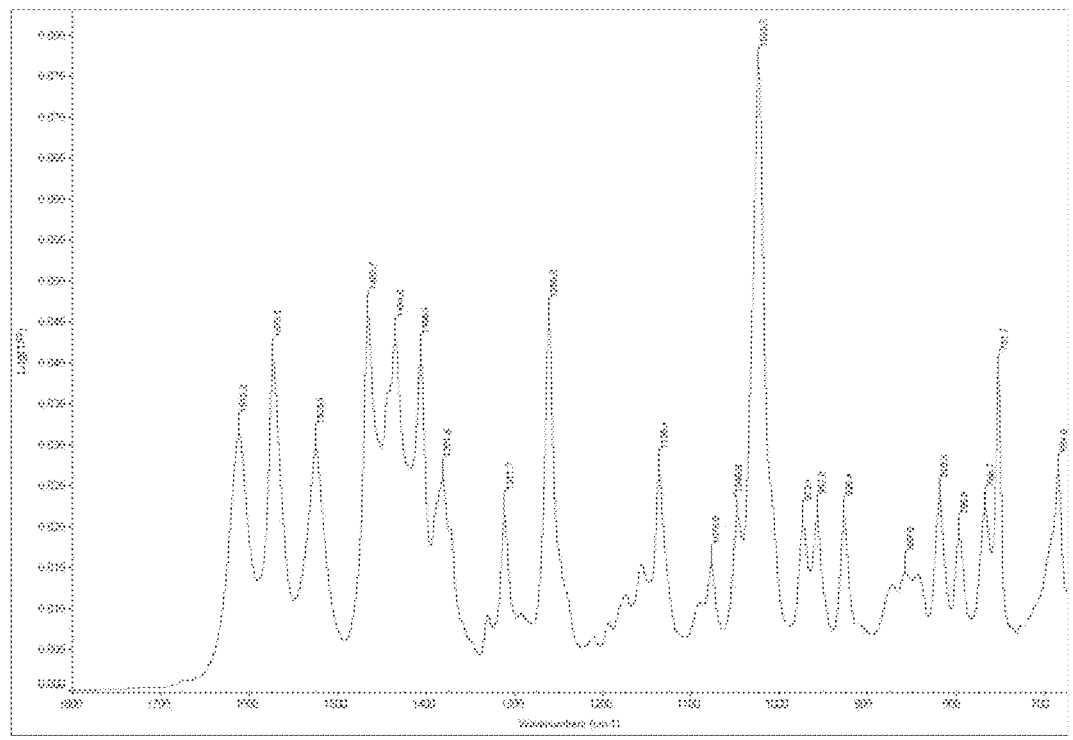
FIG. 5B is an infrared spectrum of Compound 1 Form B with spectral region of about 1800 to 675 $cm^{-1}$.

Infrared spectrum of Compound 1 Form B is shown in FIGS. 4, 5A, and 5B, respectively. In certain embodiments, Compound 1 Form B exhibits an infrared spectrum comprising peaks shown in Table 5 below.

TABLE 5

Observed Peaks from Infrared Spectrum of Compound 1 Form B

| Position (cm$^{-1}$) | Intensity (log(1/R)) |
|---|---|
| 684 | 0.0265 |
| 751.7 | 0.0394 |
| 766.7 | 0.0221 |
| 795.8 | 0.0186 |
| 818.3 | 0.0234 |
| 857 | 0.0142 |
| 926.4 | 0.0211 |
| 957 | 0.0212 |
| 973.1 | 0.0205 |
| 1023.5 | 0.0764 |
| 1046.9 | 0.0212 |
| 1076.8 | 0.0152 |
| 1136.1 | 0.0265 |
| 1260.9 | 0.0456 |
| 1311.3 | 0.0215 |
| 1381.5 | 0.0257 |
| 1406.1 | 0.0408 |
| 1434.9 | 0.0429 |
| 1465.7 | 0.0461 |
| 1525.1 | 0.0297 |
| 1573.1 | 0.0404 |
| 1612.2 | 0.0311 |
| 2838 | 0.0057 |
| 2862.1 | 0.0069 |
| 2918.9 | 0.0074 |
| 2969.8 | 0.0045 |
| 3148.7 | 0.0071 |
| 3295.9 | 0.0093 |
| 3471.4 | 0.0046 |

In certain embodiments, Compound 1 Form B exhibits an XRPD pattern comprising peaks shown in Table 6 below. Table 7 shows representative peaks for XRPD of Compound 1 Form B.

TABLE 6

Observed Peaks for XRPD Pattern of Compound 1 Form B

| 2θ (°) | d-spacing (Å) | Intensity (%) |
|---|---|---|
| (7.81-7.82) ± 0.20 | (11.298 ± 0.289-11.306 ± 0.289) | 19-22 |
| (9.09-9.10) ± 0.20 | (9.712 ± 0.213-9.723 ± 0.214) | 34-40 |
| (9.42-9.43) ± 0.20 | (9.372 ± 0.198-9.384 ± 0.199) | 33-37 |

TABLE 6-continued

Observed Peaks for XRPD Pattern of Compound 1 Form B

| 2θ (°) | d-spacing (Å) | Intensity (%) |
|---|---|---|
| (11.34-11.42) ± 0.20 | (7.744 ± 0.135-7.797 ± 0.137) | 48-49 |
| (11.93-11.94) ± 0.20 | (7.404 ± 0.124-7.411 ± 0.124) | 6-8 |
| 12.59 ± 0.20 | 7.027 ± 0.111 | 6-16 |
| (12.73-12.84) ± 0.20 | (6.891 ± 0.107-6.951 ± 0.109) | 19-22 |
| 13.41 ± 0.20 | 6.598 ± 0.098 | 19-32 |
| 14.66 ± 0.20 | 6.039 ± 0.082 | 6 |
| (14.77-14.82) ± 0.20 | (5.971 ± 0.080-5.994 ± 0.081) | 12-19 |
| 15.25 ± 0.20 | 5.806 ± 0.076 | 3 |
| (15.67-15.71) ± 0.20 | (5.638 ± 0.071-5.650 ± 0.072) | 41-54 |
| (16.04-16.10) ± 0.20 | (5.499 ± 0.068-5.520 ± 0.068) | 16-22 |
| (17.91-17.92) ± 0.20 | (4.947 ± 0.055-4.950 ± 0.055) | 48-63 |
| (18.27-18.43) ± 0.20 | (4.811 ± 0.052-4.851 ± 0.053) | 8-10 |
| 18.79 ± 0.20 | 4.719 ± 0.050 | 16 |
| (18.93-18.95) ± 0.20 | (4.680 ± 0.049-4.685 ± 0.049) | 24-25 |
| (19.38-19.39) ± 0.20 | (4.573 ± 0.047-4.576 ± 0.047) | 5-7 |
| (19.93-20.04) ± 0.20 | (4.427 ± 0.044-4.451 ± 0.044) | 100 |
| (20.92-20.95) ± 0.20 | (4.237 ± 0.040-4.243 ± 0.040) | 24-36 |
| (21.63-21.65) ± 0.20 | (4.102 ± 0.037-4.105 ± 0.037) | 6-8 |
| 22.60 ± 0.20 | 3.932 ± 0.034 | 4 |
| (23.08-23.16) ± 0.20 | (3.837 ± 0.033-3.851 ± 0.033) | 37-38 |
| (23.62-23.66) ± 0.20 | (3.757 ± 0.031-3.764 ± 0.031) | 12-16 |
| (24.57-24.70) ± 0.20 | (3.601 ± 0.029-3.620 ± 0.029) | 6-10 |
| (25.02-25.04) ± 0.20 | (3.553 ± 0.028-3.557 ± 0.028) | 37-45 |
| (25.39-25.42) ± 0.20 | (3.501 ± 0.027-3.504 ± 0.027) | 7-9 |
| (26.05-26.17) ± 0.20 | (3.402 ± 0.026-3.418 ± 0.026) | 9-11 |
| (26.69-26.74) ± 0.20 | (3.338 ± 0.025-3.331 ± 0.024) | 10-11 |
| 27.61 ± 0.20 | 3.228 ± 0.023 | 5 |
| (27.74-27.84) ± 0.20 | (3.203 ± 0.023-3.213 ± 0.023) | 7-10 |
| (28.64-28.66) ± 0.20 | (3.112 ± 0.021-3.115 ± 0.021) | 6-11 |
| 29.04 ± 0.20 | 3.072 ± 0.021 | 8 |

TABLE 7

Representative Peaks for XRPD Pattern of Compound 1 Form B

| 2θ (°) | d-spacing (Å) | Intensity (%) |
|---|---|---|
| (7.81-7.82) ± 0.20 | (11.298 ± 0.289-11.306 ± 0.289) | 19-22 |
| (9.09-9.10) ± 0.20 | (9.712 ± 0.213-9.723 ± 0.214) | 34-40 |
| (9.42-9.43) ± 0.20 | (9.372 ± 0.198-9.384 ± 0.199) | 33-37 |
| (11.34-11.42) ± 0.20 | (7.744 ± 0.135-7.797 ± 0.137) | 48-49 |
| (12.73-12.84) ± 0.20 | (6.891 ± 0.107-6.951 ± 0.109) | 19-22 |
| 13.41 ± 0.20 | 6.598 ± 0.098 | 19-32 |
| (15.67-15.71) ± 0.20 | (5.638 ± 0.071-5.650 ± 0.072) | 41-54 |
| (17.91-17.92) ± 0.20 | (4.947 ± 0.055-4.950 ± 0.055) | 48-63 |
| (18.93-18.95) ± 0.20 | (4.680 ± 0.049-4.685 ± 0.049) | 24-25 |
| (19.93-20.04) ± 0.20 | (4.427 ± 0.044-4.451 ± 0.044) | 100 |
| (20.92-20.95) ± 0.20 | (4.237 ± 0.040-4.243 ± 0.040) | 24-36 |
| (23.08-23.16) ± 0.20 | (3.837 ± 0.033-3.851 ± 0.033) | 37-38 |
| (25.02-25.04) ± 0.20 | (3.553 ± 0.028-3.557 ± 0.028) | 37-45 |

In certain embodiments, Compound 1 Form B is characterized by one or more peaks at about 19.80 to about 20.20 degrees and about 17.70 to about 18.10 degrees in X-ray powder diffraction. In certain embodiments, Compound 1 Form B is characterized by one or more peaks at about 7.6 to about 8.0 degrees, about 8.9 to about 9.3 degrees, about 9.2 to about 9.6 degrees, about 11.2 to about 11.6 degrees, about 12.6 to about 13.0 degrees, about 13.2 to about 13.6 degrees, about 15.5 to about 15.9 degrees, about 17.7 to about 18.1 degrees, about 18.7 to about 19.1 degrees, about 19.8 to about 20.2 degrees, about 20.7 to about 21.1 degrees, about 22.9 to about 23.3 degrees, and about 24.8 to about 25.2 degrees in X-ray powder diffraction.

In certain embodiments, Compound 1 Form B is characterized by its X-ray powder diffractogram that comprises peaks at about 20.0 and about 17.9020. In certain embodiments, the diffractogram further comprises one or more additional peaks selected from the following peaks at about 7.8, about 9.1, about 9.4, about 11.4, about 12.8, about 13.4, about 15.7, about 18.9, about 20.9, about 23.1, and about 25.0020. Compound 1 Form B is also characterized by its X-ray powder diffractogram as substantially shown in FIG. 3A, FIG. 3B, FIG. 3C, or FIG. 3D.

Figure 6:
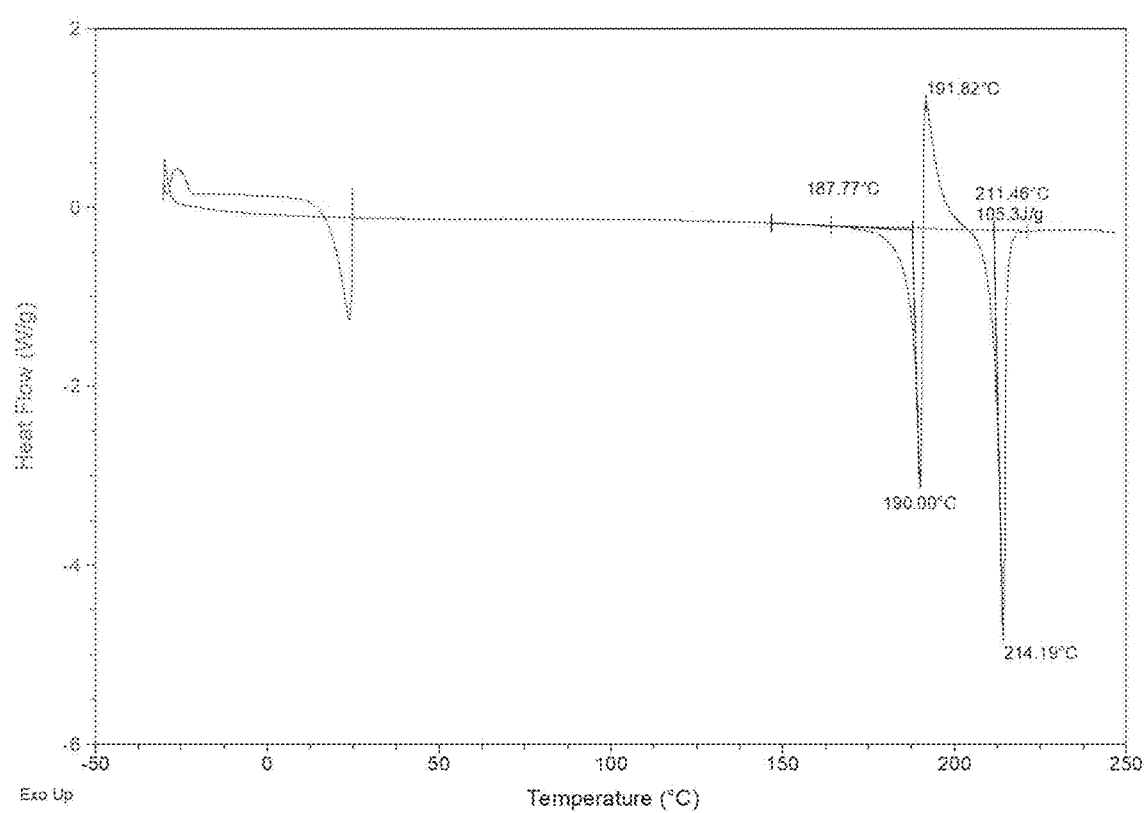
FIG. 6 is a differential scanning calorimetry thermogram of Compound 1 Form B.

In certain embodiments, Compound 1 Form B is characterized by its differential scanning calorimetry (DSC) curve that comprises an endotherm at about 188° C. or about 211° C. In certain embodiments, differential scanning calorimetry (DSC) curve of Compound 1 Form B comprises an endotherm at about 188° C. and/or about 211° C. Compound 1 Form B is also characterized by its full DSC curve as substantially as shown in FIG. 6.

Form C

The present disclosure provides a crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form C.

Figure 7:
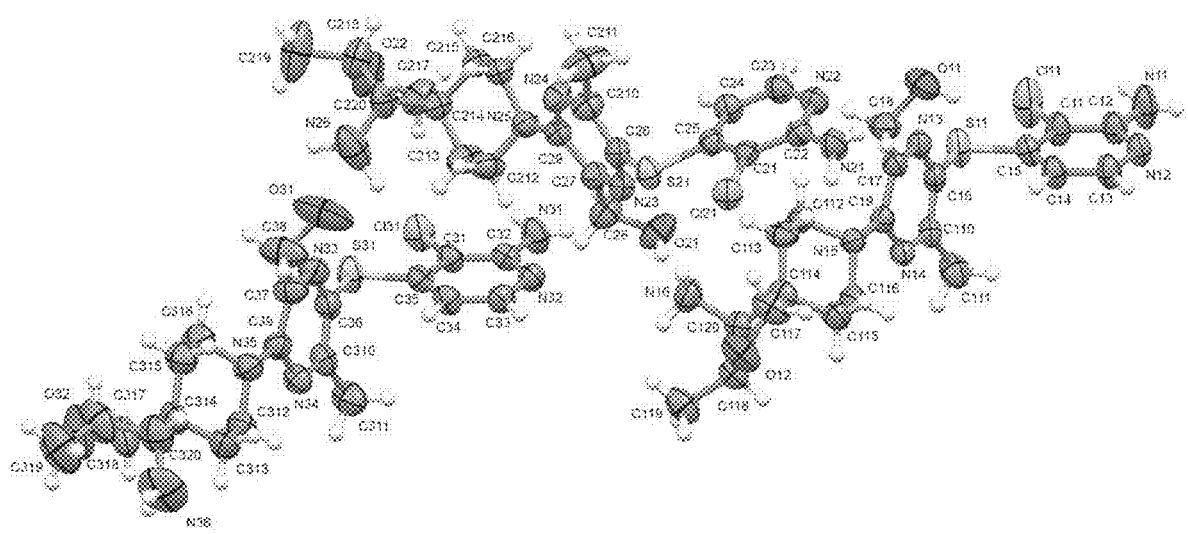
FIG. 7 is atomic ellipsoid diagram for Compound 1 Form C from a single crystal structure.

Form C is an anhydrous form that is thermodynamically stable between approximately 43 and 80° C. The unit cell parameters and calculated volume of Form C, derived from the single crystal structure, are: a=47.6458(8) Å, b=14.4005(2) Å, c=9.5460(2) Å, α=90°, β=90°, γ=90°, V=6549.8(2) Å$^3$. The space group was determined to be P2$_1$2$_1$2. The asymmetric unit shown contains three Compound 1 molecules. From the structure, the absolute configuration was determined conclusively and Compound 1 was found to bond in the S and S configuration at C120 (C220, C320) and C118 (C218, C318), respectively. FIG. 7 shows an atomic displacement ellipsoid diagram for Compound 1 Form C from single crystal structure.

In general, Compound 1 Form C is generated through spontaneous polymorphic conversion from either Compound 1 Forms D or A (or mixtures thereof) when exposed to temperatures between approximately 43° C. and 80° C.

In certain embodiments, Compound 1 Form C exhibits an XRPD pattern comprising peaks shown in Table 8 below. Table 9 shows representative peaks for XRPD pattern of Compound 1 Form C.

TABLE 8

Observed Peaks for XRPD Pattern of Compound 1 Form C

| 2θ (°) | d-spacing (Å) | Intensity (%) |
|---|---|---|
| 3.69 ± 0.20 | 23.920 ± 1.296 | 6 |
| 7.12 ± 0.20 | 12.408 ± 0.348 | 4 |
| 9.23 ± 0.20 | 9.571 ± 0.207 | 8 |
| 9.97 ± 0.20 | 8.866 ± 0.177 | 5 |
| 10.78 ± 0.20 | 8.198 ± 0.152 | 65 |
| 11.11 ± 0.20 | 7.957 ± 0.143 | 19 |
| 12.29 ± 0.20 | 7.199 ± 0.117 | 24 |
| 14.47 ± 0.20 | 6.115 ± 0.084 | 5 |
| 15.39 ± 0.20 | 5.752 ± 0.074 | 8 |
| 15.78 ± 0.20 | 5.611 ± 0.071 | 5 |
| 16.62 ± 0.20 | 5.331 ± 0.064 | 91 |
| 17.89 ± 0.20 | 4.955 ± 0.055 | 6 |
| 18.56 ± 0.20 | 4.778 ± 0.051 | 100 |
| 19.06 ± 0.20 | 4.654 ± 0.048 | 35 |
| 19.57 ± 0.20 | 4.532 ± 0.046 | 51 |
| 20.83 ± 0.20 | 4.262 ± 0.040 | 60 |
| 21.46 ± 0.20 | 4.138 ± 0.038 | 10 |
| 21.69 ± 0.20 | 4.095 ± 0.037 | 16 |
| 22.37 ± 0.20 | 3.972 ± 0.035 | 21 |
| 22.56 ± 0.20 | 3.939 ± 0.034 | 22 |
| 23.22 ± 0.20 | 3.828 ± 0.033 | 20 |
| 23.55 ± 0.20 | 3.774 ± 0.032 | 10 |
| 24.69 ± 0.20 | 3.603 ± 0.029 | 6 |
| 25.04 ± 0.20 | 3.554 ± 0.028 | 8 |
| 25.61 ± 0.20 | 3.475 ± 0.027 | 33 |

TABLE 8-continued

Observed Peaks for XRPD Pattern of Compound 1 Form C

| 2θ (°) | d-spacing (Å) | Intensity (%) |
|---|---|---|
| 25.84 ± 0.20 | 3.446 ± 0.026 | 12 |
| 26.44 ± 0.20 | 3.369 ± 0.025 | 6 |
| 27.26 ± 0.20 | 3.268 ± 0.024 | 18 |
| 28.04 ± 0.20 | 3.180 ± 0.022 | 11 |

TABLE 9

Representative Peaks for XRPD Pattern of Compound 1 Form C

| 2θ (°) | d-spacing (Å) | Intensity (%) |
|---|---|---|
| 10.78 ± 0.20 | 8.198 ± 0.152 | 65 |
| 11.11 ± 0.20 | 7.957 ± 0.143 | 19 |
| 12.29 ± 0.20 | 7.199 ± 0.117 | 24 |
| 16.62 ± 0.20 | 5.331 ± 0.064 | 91 |
| 18.56 ± 0.20 | 4.778 ± 0.051 | 100 |
| 19.06 ± 0.20 | 4.654 ± 0.048 | 35 |
| 19.57 ± 0.20 | 4.532 ± 0.046 | 51 |
| 20.83 ± 0.20 | 4.262 ± 0.040 | 60 |
| 25.61 ± 0.20 | 3.475 ± 0.027 | 33 |

In certain embodiments, Compound 1 Form C is characterized by one or more peaks at about 18.30 to about 18.70 degrees and about 16.40 to about 16.80 degrees in X-ray powder diffraction. In certain embodiments, Compound 1 Form C is characterized by one or more peaks at about 10.60 to about 11.00 degrees, about 10.90 to about 11.30 degrees, about 12.10 to about 12.50 degrees, about 16.40 to about 16.80 degrees, about 18.30 to about 18.70 degrees, about 18.80 to about 19.20 degrees, about 19.40 to about 19.80 degrees, about 20.60 to about 21.00 degrees, and about 25.40 to about 25.70 degrees in X-ray powder diffraction.

In certain embodiments, Compound 1 Form C is characterized by its X-ray powder diffractogram that comprises peaks at about 18.56 and about 16.62°2θ. In certain embodiments, the diffractogram further comprises one or more additional peaks selected from the following peaks at about 10.78, about 11.11, about 12.29, about 19.06, about 19.57, about 20.83, and about 25.61°2θ. Compound 1 Form C is also characterized by its X-ray powder diffractogram as substantially shown in FIG. 8A or FIG. 8B.

Form D

The present disclosure provides a crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form D.

Figure 9:
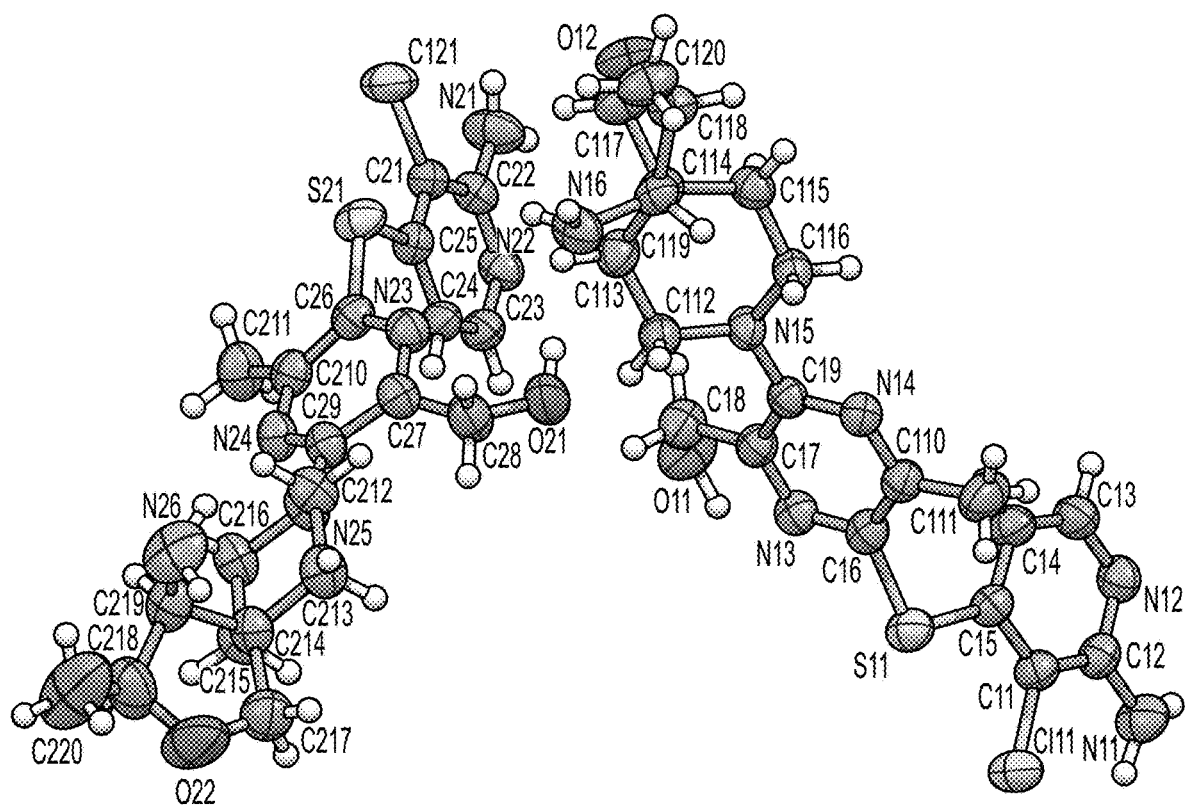
FIG. 9 is atomic ellipsoid diagram for Compound 1 Form D from a single crystal structure.

Compound 1 Form D is an anhydrous form that is thermodynamically stable below approximately 43° C. The unit cell parameters and calculated volume of Compound Form D, derived from the single crystal structure, are: a=14.0679(4) Å, b=16.0057(4) Å, c=19.1837(6) Å, α=90°, β=90°, γ=90°, V=4319.5(2) Å$^3$. The space group was determined to be P2$_1$2$_1$2. The asymmetric unit shown contains three Compound 1 molecules. From the structure, the absolute configuration was determined conclusively and Compound 1 was found to bond in the S and S configuration at C120 (C220, C320) and C118 (C218, C318), respectively. FIG. 9 shows an atomic displacement ellipsoid diagram for Compound 1 Form D from single crystal structure.

The differential scanning calorimetry thermogram of Compound 1 Form D exhibits multiple endotherms at approximately 51, 90, and 213° C. (onset temperatures). These events correlate respectively with the phase transition to Compound 1 Form C, another phase transition to Compound 1 Form A, and the melt Compound 1 Form A.

Figure 11:
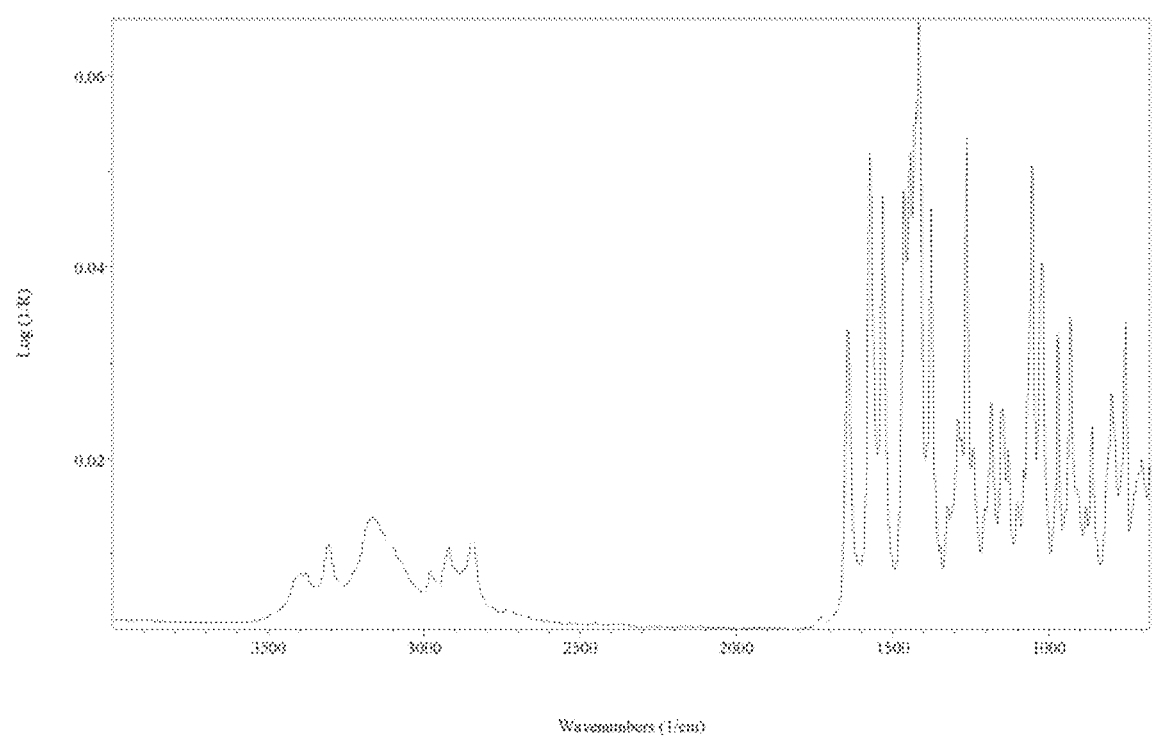
FIG. 11 is an infrared spectrum of Compound 1 Form D.
Figure 12A:
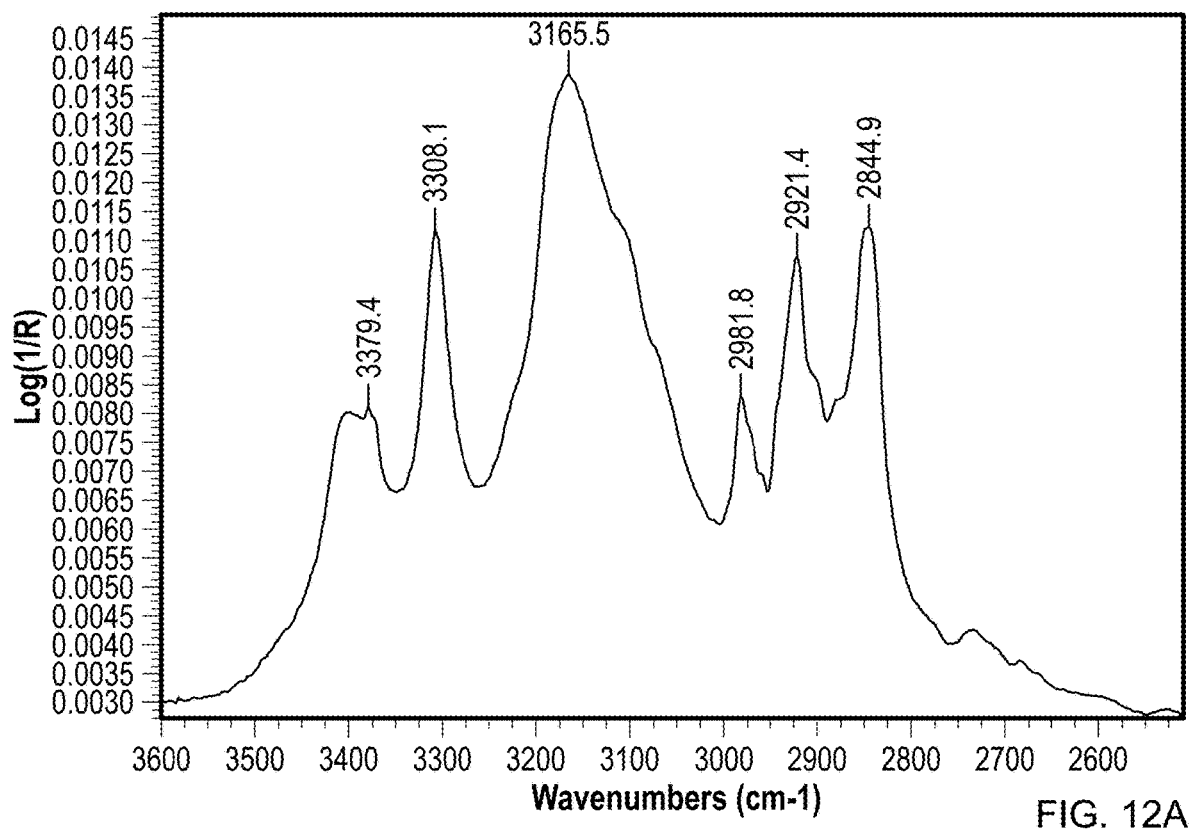
FIG. 12A is an infrared spectrum of Compound 1 Form D with spectral region of about 3600 to 2500 $cm^{-1}$.
Figure 12B:
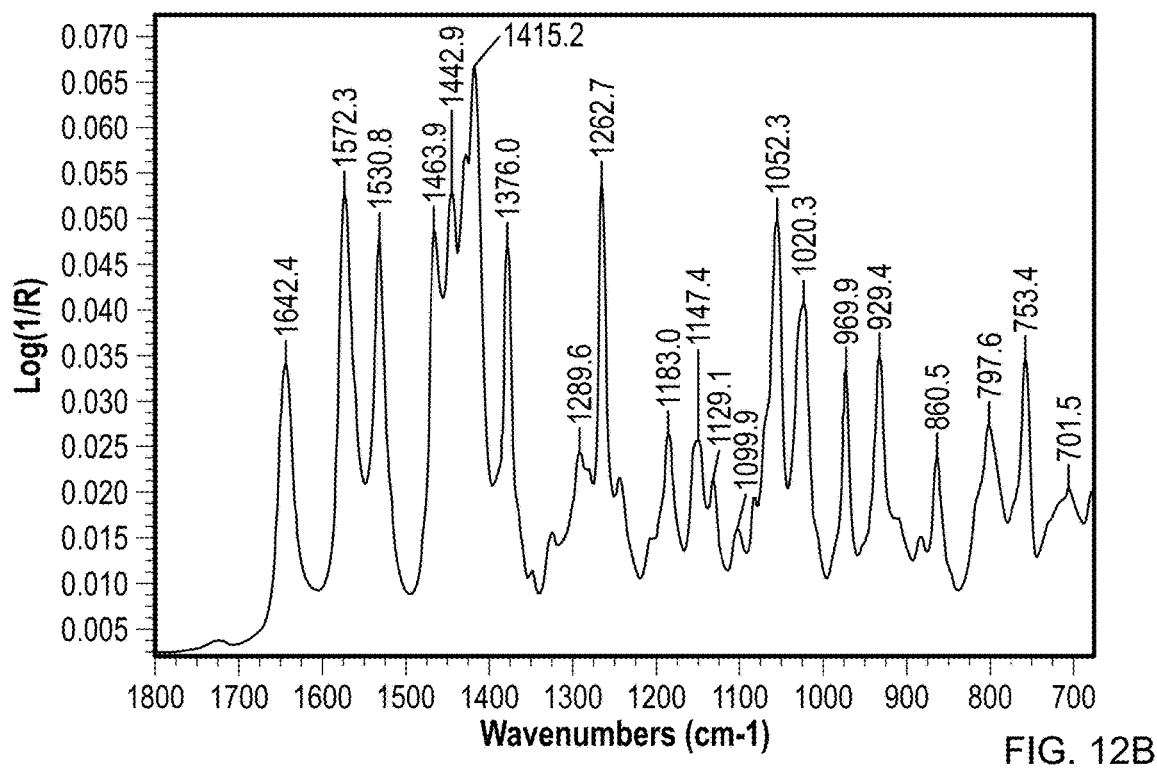
FIG. 12B is an infrared spectrum of Compound 1 Form D with spectral region of about 1800 to 675 $cm^{-1}$.

Infrared spectrum of Compound 1 Form D is shown in FIGS. 11, 12A, and 12B, respectively. In certain embodiments, Compound 1 Form D exhibits an infrared spectrum comprising peaks shown in Table 10 below.

TABLE 10

Observed Peaks from Infrared Spectrum of Compound 1 Form D

| Position (cm$^{-1}$) | Intensity (log(1/R)) |
|---|---|
| 701.5 | 0.0201 |
| 753.4 | 0.0344 |
| 797.6 | 0.027 |
| 860.5 | 0.0235 |
| 929.4 | 0.0348 |
| 969.9 | 0.0333 |
| 1020.3 | 0.0405 |
| 1052.3 | 0.051 |
| 1099.9 | 0.0156 |
| 1129.1 | 0.0211 |
| 1147.4 | 0.0252 |
| 1183 | 0.0261 |
| 1262.7 | 0.0538 |
| 1289.6 | 0.0242 |
| 1376 | 0.0473 |
| 1415.2 | 0.066 |
| 1442.9 | 0.0521 |
| 1463.9 | 0.0482 |
| 1530.8 | 0.0476 |
| 1572.3 | 0.052 |
| 1642.4 | 0.0336 |
| 2844.9 | 0.0112 |
| 2921.4 | 0.0107 |
| 2981.8 | 0.0083 |
| 3165.5 | 0.0139 |
| 3308.1 | 0.0112 |
| 3379.4 | 0.0081 |

In certain embodiments, Compound 1 Form D exhibits an XRPD pattern comprising peaks shown in Table 11 below. Table 12 shows representative peaks for XRPD pattern of Compound 1 Form D.

TABLE 11

Observed Peaks for XRPD Pattern of Compound 1 Form D

| 2θ (°) | d-spacing (Å) | Intensity (%) |
|---|---|---|
| 7.16 ± 0.20 | 12.337 ± 0.344 | 6 |
| 9.20 ± 0.20 | 9.602 ± 0.208 | 8 |
| 10.73 ± 0.20 | 8.239 ± 0.153 | 62 |
| 11.03 ± 0.20 | 8.012 ± 0.145 | 15 |
| 11.15 ± 0.20 | 7.930 ± 0.142 | 14 |
| 12.58 ± 0.20 | 7.030 ± 0.111 | 17 |
| 13.50 ± 0.20 | 6.551 ± 0.097 | 4 |
| 14.51 ± 0.20 | 6.101 ± 0.084 | 6 |
| 14.90 ± 0.20 | 5.941 ± 0.079 | 5 |
| 15.20 ± 0.20 | 5.824 ± 0.076 | 3 |
| 15.62 ± 0.20 | 5.667 ± 0.072 | 8 |
| 16.18 ± 0.20 | 5.472 ± 0.067 | 4 |
| 16.77 ± 0.20 | 5.282 ± 0.063 | 71 |
| 17.22 ± 0.20 | 5.145 ± 0.059 | 4 |
| 17.41 ± 0.20 | 5.091 ± 0.058 | 4 |
| 17.75 ± 0.20 | 4.992 ± 0.056 | 4 |
| 18.48 ± 0.20 | 4.797 ± 0.051 | 100 |
| 19.01 ± 0.20 | 4.664 ± 0.049 | 14 |
| 19.17 ± 0.20 | 4.626 ± 0.048 | 41 |
| 19.54 ± 0.20 | 4.539 ± 0.046 | 69 |
| 20.04 ± 0.20 | 4.427 ± 0.044 | 4 |
| 20.31 ± 0.20 | 4.370 ± 0.043 | 3 |
| 20.88 ± 0.20 | 4.251 ± 0.040 | 50 |
| 21.40 ± 0.20 | 4.150 ± 0.038 | 11 |
| 21.58 ± 0.20 | 4.114 ± 0.038 | 12 |

TABLE 11-continued

Observed Peaks for XRPD Pattern of Compound 1 Form D

| 2θ (°) | d-spacing (Å) | Intensity (%) |
|---|---|---|
| 21.82 ± 0.20 | 4.069 ± 0.037 | 8 |
| 22.47 ± 0.20 | 3.953 ± 0.035 | 37 |
| 22.87 ± 0.20 | 3.886 ± 0.034 | 9 |
| 23.09 ± 0.20 | 3.849 ± 0.033 | 18 |
| 23.54 ± 0.20 | 3.776 ± 0.032 | 3 |
| 23.85 ± 0.20 | 3.728 ± 0.031 | 6 |
| 24.67 ± 0.20 | 3.606 ± 0.029 | 3 |
| 24.94 ± 0.20 | 3.568 ± 0.028 | 5 |
| 25.59 ± 0.20 | 3.478 ± 0.027 | 25 |
| 25.73 ± 0.20 | 3.460 ± 0.026 | 15 |
| 26.00 ± 0.20 | 3.424 ± 0.026 | 5 |
| 26.45 ± 0.20 | 3.367 ± 0.025 | 4 |
| 27.02 ± 0.20 | 3.298 ± 0.024 | 6 |
| 27.24 ± 0.20 | 3.271 ± 0.024 | 14 |
| 27.71 ± 0.20 | 3.216 ± 0.023 | 5 |
| 27.88 ± 0.20 | 3.197 ± 0.022 | 8 |
| 28.45 ± 0.20 | 3.134 ± 0.022 | 5 |
| 28.60 ± 0.20 | 3.119 ± 0.021 | 4 |
| 28.93 ± 0.20 | 3.084 ± 0.021 | 6 |
| 29.17 ± 0.20 | 3.059 ± 0.021 | 9 |

TABLE 12

Representative Peaks for XRPD Pattern of Compound 1 Form D

| 2θ (°) | d-spacing (Å) | Intensity (%) |
|---|---|---|
| 10.73 ± 0.20 | 8.239 ± 0.153 | 62 |
| 11.03 ± 0.20 | 8.012 ± 0.145 | 15 |
| 11.15 ± 0.20 | 7.930 ± 0.142 | 14 |
| 12.58 ± 0.20 | 7.030 ± 0.111 | 17 |
| 16.77 ± 0.20 | 5.282 ± 0.063 | 71 |
| 18.48 ± 0.20 | 4.797 ± 0.051 | 100 |
| 19.17 ± 0.20 | 4.626 ± 0.048 | 41 |
| 19.54 ± 0.20 | 4.539 ± 0.046 | 69 |
| 20.88 ± 0.20 | 4.251 ± 0.040 | 50 |
| 22.47 ± 0.20 | 3.953 ± 0.035 | 37 |
| 25.59 ± 0.20 | 3.478 ± 0.027 | 25 |

In certain embodiments, Compound 1 Form D is characterized by one or more peaks at about 18.30 to about 18.70 degrees and about 16.50 to about 16.80 degrees in X-ray powder diffraction. In certain embodiments, Compound 1 Form D is characterized by one or more peaks at about 10.50 to about 10.90 degrees, about 10.80 to about 11.20 degrees, about 10.90 to about 11.30 degrees, about 12.40 to about 12.80 degrees, about 16.50 to about 16.80 degrees, about 18.30 to about 18.70 degrees, about 19.00 to about 19.40 degrees, about 19.30 to about 19.70 degrees, about 20.70 to about 21.10 degrees, about 22.30 to about 22.70 degrees, and about 25.40 to about 25.80 degrees in X-ray powder diffraction.

In certain embodiments, Compound 1 Form D is characterized by its X-ray powder diffractogram that comprises peaks at about 18.48 and about 16.77° 2θ. In certain embodiments, the diffractogram further comprises one or more additional peaks selected from the following peaks at about 10.73, about 11.03, about 11.15, about 12.58, about 19.17, about 19.54, about 20.88, about 22.47, and about 25.59° 2θ. Compound 1 Form D is also characterized by its X-ray powder diffractogram as substantially shown in FIG. 10A or FIG. 10B.

Figure 13:
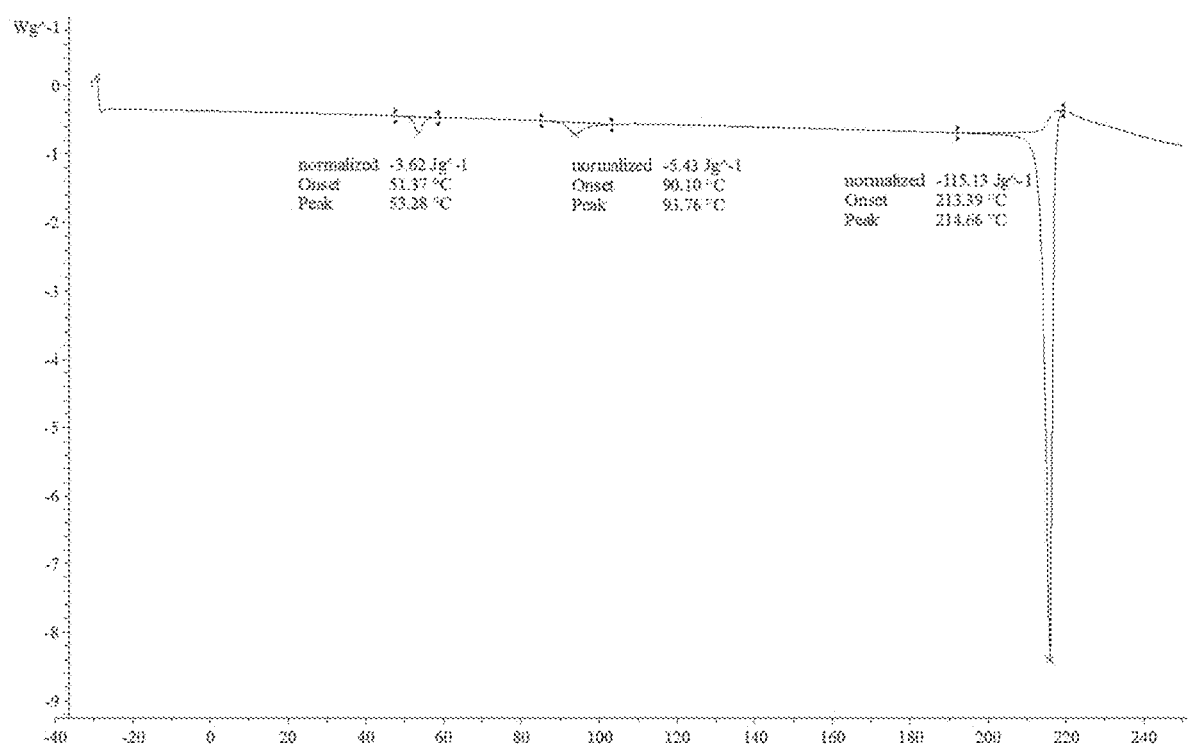
FIG. 13 is a differential scanning calorimetry thermogram of Compound 1 Form D.

In certain embodiments, Compound 1 Form D is characterized by its differential scanning calorimetry (DSC) curve that comprises an endotherm at about 51° C., 90° C., or 211° C. Compound 1 Form D is also characterized by its full DSC curve as substantially as shown in FIG. 13.

Methods of Preparation Compounds and Compositions

The compounds of the present disclosure may be made by a variety of methods, including standard chemistry. Suitable synthetic routes are depicted in the schemes given below.

The compounds of the formula described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of the present disclosure.

Preparation of Compounds

The compounds described herein may be made from commercially available starting materials or synthesized using known organic, inorganic, and/or enzymatic processes.

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. These methods include but are not limited to those methods described below.

Methods for preparing Compound 1 prior to crystallization is described in WO 2018/013597, the entire contents of which are incorporated herein by reference.

In certain embodiments, a slurry of Compound 1 in methanol is stirred at ~58° C. for ~9 days. Compound 1 Form A is recovered from the slurry by water aspirator vacuum filtration.

In certain embodiments, a solution of Compound 1 in dichloromethane or methanol is generated at ambient temperature and filtered with a 0.2-μm nylon filter. The filtrates are left to evaporate under ambient conditions to provide Compound 1 Form B.

In certain embodiments, a solution of Compound 1 in methanol is generated at approximately 50° C., treated with activated charcoal, and filtered. The filtrate is slowly cooled to ambient temperature to provide crystals of Compound 1 Form B.

In certain embodiments, a slurry of Compound 1 in methanol is heated to reflux and filtered by water aspirator vacuum filtration. The filtrate is returned to boil, treated with activated charcoal, and filtered again by water aspirator vacuum filtration. The filtrate is rotary evaporated to dryness, briefly triturated in diethyl ether, filtered by water aspirator vacuum filtration, and dried under nitrogen. The solids are used to generate a slurry in methanol and stirred at ~58° C. for ~6 days to provide crystals of Compound 1 Form C.

In certain embodiments, a slurry of Compound 1 in methanol is heated to reflux and filtered by water aspirator vacuum filtration. The filtrate is treated with activated charcoal and filtered again by water aspirator vacuum filtration. The activated charcoal treatment with filtration is repeated three times. The volume of the filtrate is reduced to less than a quarter of the original volume under a purge of nitrogen, providing solids. The solids are harvested by water aspirator vacuum filtration and washed with methanol. A slurry of the solids in methanol was stirred at ambient temperature for ~14 days. Compound 1 Form D is recovered from the slurry by water aspirator vacuum filtration.

In certain embodiments, a slurry of Compound 1 in methanol is heated to reflux and filtered by water aspirator vacuum filtration. The filtrate is returned to boil, treated with activated charcoal, and filtered again by water aspirator vacuum filtration. The filtrate is rotary evaporated to dryness, briefly triturated in diethyl ether, filtered by water aspirator vacuum filtration, and dried under nitrogen. Particles from the resulting solids are heated in mineral oil until crystals in the shape of geometric plates formed. The crystals are left in the mineral oil for ~1 month at ambient temperature and allowed to convert to Compound 1 Form D before isolating.

Methods of Using the Disclosed Compounds and Compositions

Methods and Uses of the Disclosure

Another aspect of the disclosure relates to a method of treating a disease associated with SHP2 modulation in a subject in need thereof. The method involves administering to a patient in need of treatment for diseases or disorders associated with SHP2 modulation an effective amount of one or more compounds of the present disclosure (e.g., Compound 1 Form A, Compound 1 Form B, Compound 1 Form C, or Compound 1 Form D, and pharmaceutically acceptable salts thereof), or of one or more pharmaceutical compositions of the present disclosure. In some embodiments, the disease can be, but is not limited to Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In addition, SHP2 plays a role in transducing signals originating from immune checkpoint molecules, including but not limited to programmed cell death protein 1 (PD-1) and cytotoxic T-lymphocyte-associated protein 4 (CTLA-4). In this context, modulation of SHP2 function can lead to immune activation, specifically anti-cancer immune responses.

Another aspect of the disclosure is directed to a method of inhibiting SHP2. The method involves administering to a patient in need thereof an effective amount of one or more compounds of the present disclosure (e.g., Compound 1 Form A, Compound 1 Form B, Compound 1 Form C, or Compound 1 Form D, and pharmaceutically acceptable salts thereof), or of one or more pharmaceutical compositions of the present disclosure.

The present disclosure relates to compounds or compositions disclosed herein that are capable of modulating the activity of (e.g., inhibiting) SHP2. The present disclosure also relates to the therapeutic use of such compounds and compositions.

One or more disclosed compounds or compositions can be administered in effective amounts to treat or prevent a disorder and/or prevent the development thereof in subjects. In some embodiments, SHP2 is inhibited after treatment with less than 1000 nM of a compound of the disclosure. In some embodiments, SHP2 is inhibited after treatment with about 10 nM to about 100 nM of a compound of the disclosure. In some embodiments, SHP2 is inhibited after treatment with about 10 nM to about 100 nM of a compound of the disclosure. In some embodiments, SHP2 is inhibited after treatment with less than 10 nM of a compound of the disclosure.

Another aspect of the present disclosure relates to one or more compounds of the present disclosure (e.g., Compound 1 Form A, Compound 1 Form B, Compound 1 Form C, or Compound 1 Form D, and pharmaceutically acceptable salts thereof), or one or more compositions of the present disclosure for use in treating or preventing a disease associated with SHP2 modulation. In some embodiments, the disease is Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In another aspect, the present disclosure relates to the use of one or more compounds of the present disclosure (e.g., Compound 1 Form A, Compound 1 Form B, Compound 1 Form C, or Compound 1 Form D, and pharmaceutically acceptable salts thereof), in the manufacture of a medicament for treating or preventing a disease. In some embodiments, the disease is associated with SHP2 modulation.

In another aspect, the present disclosure relates to one or more compounds of the present disclosure (e.g., Compound 1 Form A, Compound 1 Form B, Compound 1 Form C, or Compound 1 Form D, and pharmaceutically acceptable salts thereof), for use as a medicament. In some embodiments, the medicament is used for treating or preventing a disease associated with SHP2 modulation.

In one aspect, the present disclosure relates to one or more compositions comprising one or more compounds of the present disclosure (e.g., Compound 1 Form A, Compound 1 Form B, Compound 1 Form C, or Compound 1 Form D, and pharmaceutically acceptable salts thereof), for use as a medicament. In some embodiments, the medicament is used for treating or preventing a disease associated with SHP2 modulation.

Pharmaceutical Compositions and Modes of Administration of the Disclosure

Another aspect of the present disclosure relates to pharmaceutical compositions comprising one or more crystalline forms of the present disclosure and a pharmaceutically acceptable carrier. The pharmaceutically acceptable carrier can further include an excipient, diluent, or surfactant.

In certain embodiments, the present disclosure provides a pharmaceutical composition comprising at least two crystalline forms selected from Compound 1 Form A, or a pharmaceutically acceptable salt thereof; Compound 1 Form B, or a pharmaceutically acceptable salt thereof, Compound 1 Form C, or a pharmaceutically acceptable salt thereof, and Compound 1 Form D, or a pharmaceutically acceptable salt thereof; and a pharmaceutically acceptable carrier.

In certain embodiments, the present disclosure provides a pharmaceutical composition comprising Compound 1 Form D, or a pharmaceutically acceptable salt thereof, and Compound 1 Form A, or a pharmaceutically acceptable salt thereof, and a pharmaceutically acceptable carrier. In certain embodiments, the present disclosure provides a pharmaceutical composition comprising Compound 1 Form D, or a pharmaceutically acceptable salt thereof, and Compound 1 Form B, or a pharmaceutically acceptable salt thereof, and a pharmaceutically acceptable carrier. In certain embodiments, the present disclosure provides a pharmaceutical composition comprising Compound 1 Form D, or a pharmaceutically acceptable salt thereof, and Compound 1 Form C, or a pharmaceutically acceptable salt thereof, and a pharmaceutically acceptable carrier.

In certain embodiments, the present disclosure provides a pharmaceutical composition comprising Compound 1 Form C, or a pharmaceutically acceptable salt thereof, and Compound 1 Form A, or a pharmaceutically acceptable salt thereof, and a pharmaceutically acceptable carrier. In certain embodiments, the present disclosure provides a pharmaceutical composition comprising Compound 1 Form C, or a pharmaceutically acceptable salt thereof, and Compound 1 Form B, or a pharmaceutically acceptable salt thereof, and a pharmaceutically acceptable carrier. In certain embodiments, the present disclosure provides a pharmaceutical composition comprising Compound 1 Form C, or a pharmaceutically acceptable salt thereof, and Compound 1 Form D, or a pharmaceutically acceptable salt thereof, and a pharmaceutically acceptable carrier.

In certain embodiments, the present disclosure provides a pharmaceutical composition comprising Compound 1 Form B, or a pharmaceutically acceptable salt thereof, and Compound 1 Form A, or a pharmaceutically acceptable salt thereof, and a pharmaceutically acceptable carrier. In certain embodiments, the present disclosure provides a pharmaceutical composition comprising Compound 1 Form B, or a pharmaceutically acceptable salt thereof, and Compound 1 Form C, or a pharmaceutically acceptable salt thereof, and a pharmaceutically acceptable carrier. In certain embodiments, the present disclosure provides a pharmaceutical composition comprising Compound 1 Form B, or a pharmaceutically acceptable salt thereof, and Compound 1 Form D, or a pharmaceutically acceptable salt thereof, and a pharmaceutically acceptable carrier.

In certain embodiments, the present disclosure provides a pharmaceutical composition comprising Compound 1 Form A, or a pharmaceutically acceptable salt thereof, and Compound 1 Form B, or a pharmaceutically acceptable salt thereof, and a pharmaceutically acceptable carrier. In certain embodiments, the present disclosure provides a pharmaceutical composition comprising Compound 1 Form A, or a pharmaceutically acceptable salt thereof, and Compound 1 Form C, or a pharmaceutically acceptable salt thereof, and a pharmaceutically acceptable carrier. In certain embodiments, the present disclosure provides a pharmaceutical composition comprising Compound 1 Form A, or a pharmaceutically acceptable salt thereof, and Compound 1 Form D, or a pharmaceutically acceptable salt thereof, and a pharmaceutically acceptable carrier.

Compositions can be prepared according to conventional mixing, granulating, filling, encapsulation, compression, solvent-casting or coating methods, respectively, and the present pharmaceutical compositions can contain from about 0.1% to about 99%, from about 5% to about 90%, or from about 1% to about 20% of the disclosed compound by weight or volume.

Administration of the disclosed compounds and pharmaceutical compositions can be accomplished via any mode of administration for therapeutic agents. These modes include systemic or local administration such as oral, nasal, parenteral, intravenous, transdermal, subcutaneous, vaginal, buccal, rectal or topical administration modes.

Depending on the intended mode of administration, the disclosed compounds or pharmaceutical compositions can be in solid, semi-solid or liquid dosage form, in an immediate release or modified-release form, such as, for example, injectables, tablets, suppositories, pills, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets comprising one or more compounds of the present disclosure and a pharmaceutically acceptable carrier, such as, but not limited to, a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, one or more disclosed compounds are dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

One or more disclosed compounds or compositions can be also formulated as a suppository that can be prepared from fatty emulsions or suspensions; using polyalkylene glycols such as propylene glycol, as the carrier.

One or more disclosed compounds or compositions can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

One or more disclosed compounds or compositions can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxy propylmethacrylamide-phenol, polyhydroxyethylaspanamidephenol, or polyethyleneoxide polylysine substituted with palmitoyl residues. Furthermore, the one or more disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In some embodiments, one or more disclosed compounds are not covalently bound to a polymer, e.g., a polycarboxylic acid polymer, or a polyacrylate.

One or more disclosed compounds or compositions can be delivered by parental administration. Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Dosage Regimens of the Disclosure

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In some embodiments, the compositions are in the form of a tablet that can be scored.

If desired, the effective daily dose of one or more compounds or compositions of this disclosure may be administered as one, two, three, four, five, six, or more sub-doses administered separately at appropriate intervals throughout the day, optionally, in unit dosage forms. In some embodiments of this disclosure, the one or more compounds or compositions of this disclosure, or mixtures thereof, may be administered two or three times daily. In some embodiments, the one or more compounds or compositions of this disclosure will be administered once daily.

In some embodiments, one or more compounds or compositions described herein may be used alone or together or conjointly administered, or used in combination, with another type of therapeutic agent. Conjoint administration or used in combination refers to any form of administration of two or more different therapeutic compounds or compositions such that the second compound or composition is administered while the previously administered therapeutic compound or composition is still effective in the body. For example, the different therapeutic compounds or compositions can be administered either in the same formulation or in a separate formulation, either simultaneously, sequentially, or by separate dosing of the individual components of the treatment. In some embodiments, the different therapeutic compounds or compositions can be administered within one hour, 12 hours, 24 hours, 36 hours, 48 hours, 72 hours, or a week of one another. Thus, an individual who receives such treatment can benefit from a combined effect of different therapeutic compounds or compositions.

Kits

In some embodiments, this disclosure also provides a pharmaceutical package or kit comprising one or more containers filled with at least one compound or composition of this disclosure. Optionally associated with such a container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both. In some embodiments, the kit comprises at least two containers, at least one of which contains at least one compound or composition of this disclosure. In some embodiments, the kit contains at least two containers, and each of the at least two containers contains at least one compound or composition of this disclosure.

In some embodiments, the kit includes additional materials to facilitate delivery of the subject compounds and compositions. For example, the kit may include one or more of a catheter, tubing, infusion bag, syringe, and the like. In some embodiments, the compounds and compositions are packaged in a lyophilized form, and the kit includes at least two containers: a container comprising the lyophilized compounds or compositions and a container comprising a suitable amount of water, buffer, or other liquid suitable for reconstituting the lyophilized material.

The foregoing applies to any of the compounds, compositions, methods, and uses described herein. This disclosure specifically contemplates any combination of the features of such compounds, compositions, methods, and uses (alone or in combination) with the features described for the various kits described in this section.

Exemplary Embodiments

Some embodiments of this disclosure are Embodiment I, as follows:

Embodiment I-1. A crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form D.

Embodiment I-2. The crystalline form of Embodiment I-1, wherein an X-ray powder diffraction pattern comprises 2θ values: about 18.48 and about 16.77.

Embodiment I-3. The crystalline form of Embodiment I-2, wherein the X-ray powder diffraction pattern further comprises one or more 2θ values at about: 10.73, 11.03, 11.15, 12.58, 19.17, 19.54, 20.88, 22.47, and 25.59.

Embodiment I-4. The crystalline form of Embodiment I-1, wherein the X-ray powder diffraction pattern is substantially in accordance with that shown in FIG. 10A.

Embodiment I-5. The crystalline form of any one of Embodiments I-1 to I-4, wherein a differential scanning calorimetry (DSC) curve comprises an endotherm at about 51° C., about 90° C., or about 211° C.

Embodiment I-6. The crystalline form of any one of Embodiments I-1 to I-4, wherein the DSC curve is substantially as shown in FIG. 13.

Embodiment I-7. The crystalline form of any one of Embodiments I-1 to I-6, having the unit cell dimensions: a=14.0679(4) Å, b=16.0057(4) Å, c=19.1837(6) Å, α=90°, β=90°, γ=90°; cell volume (V) of 4319.5(2) Å$^3$; and a space group of P2$_1$2$_1$2 space group.

Embodiment I-8. A crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form B.

Embodiment I-9. The crystalline form of Embodiment I-8, wherein an X-ray powder diffraction pattern comprises 2θ values: about 20.0 and about 17.9.

Embodiment I-10. The crystalline form of Embodiment I-9, wherein the X-ray powder diffraction pattern further comprises one or more 2θ values at about: 7.8, 9.1, 9.4, 11.4, 12.8, 13.4, 15.7, 18.9, 20.9, 23.1, and 25.0.

Embodiment I-11. The crystalline form of Embodiment I-8, wherein the X-ray powder diffraction pattern is substantially in accordance with that shown in FIG. 3A.

Embodiment I-12. The crystalline form of any one of Embodiments I-8 to I-11, wherein a differential scanning calorimetry (DSC) curve comprises an endotherm at about 188° C. and/or about 211° C.

Embodiment I-13. The crystalline form of any one of Embodiments I-8 to I-11, wherein the DSC curve is substantially as shown in FIG. 6.

Embodiment I-14. The crystalline form of any one of Embodiments I-8 to I-11, having the unit cell dimensions: a=9.65334(16) Å, b=10.28825(18) Å, c=11.62614(19) Å, α=76.0621(15°), β=89.6714(13°), γ=76.4043(15°); cell volume (V) of 1087.68(3) Å$^3$; and a space group of P1 space group.

Embodiment I-15. A crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form C.

Embodiment I-16. The crystalline form of Embodiment I-15, wherein an X-ray powder diffraction pattern comprises 2θ values: about 18.56 and about 16.62.

Embodiment I-17. The crystalline form of Embodiment I-16, wherein the X-ray powder diffraction pattern further comprises one or more 2θ values at about: 10.78, 11.11, 12.29, 19.06, 19.57, 20.83, and 25.61.

Embodiment I-18. The crystalline form of Embodiment I-15, wherein the X-ray powder diffraction pattern is substantially in accordance with that shown in FIG. 8A.

Embodiment I-19. The crystalline form of any one of Embodiments I-15 to I-18, having the unit cell dimensions: a=47.6458(8) Å, b=14.4005(2) Å, c=9.5460(2) Å, α=90°, β=90°, γ=90°; cell volume (V) of 6549.8(2) Å$^3$; and a space group of P2$_1$2$_1$2.

Embodiment I-20. A crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form A.

Embodiment I-21. The crystalline form of Embodiment I-20, wherein an X-ray powder diffraction pattern comprises 2θ values: about 16.66 and about 18.50.

Embodiment I-22. The crystalline form of Embodiment I-21, wherein the X-ray powder diffraction pattern further comprises one or more 2θ values at about: 10.76, 11.11, 12.35, 19.08, 19.52, 20.85, and 25.63.

Embodiment I-23. The crystalline form of Embodiment I-20, wherein the X-ray powder diffraction pattern is substantially in accordance with that shown in FIG. 1A.

Embodiment I-24. The crystalline form of Embodiment I-20, having an onset melting temperature of about 213° C.

Embodiment I-25. A pharmaceutical composition comprising the crystalline form of any one of Embodiments I-1 to I-24, or a pharmaceutically acceptable salt thereof, and a pharmaceutically acceptable carrier.

Embodiment I-26. A pharmaceutical composition of Embodiment I-25, wherein the pharmaceutical composition comprises Compound 1 Form D, or a pharmaceutically acceptable salt thereof, and a pharmaceutically acceptable carrier.

Embodiment I-27. A pharmaceutical composition of Embodiment I-25, wherein the pharmaceutical composition comprises Compound 1 Form C, or a pharmaceutically acceptable salt thereof, and a pharmaceutically acceptable carrier.

Embodiment I-28. A pharmaceutical composition of Embodiment I-25, wherein the pharmaceutical composition comprises Compound 1 Form B, or a pharmaceutically acceptable salt thereof, and a pharmaceutically acceptable carrier.

Embodiment I-29. A pharmaceutical composition of Embodiment I-25, wherein the pharmaceutical composition comprises Compound 1 Form A, or a pharmaceutically acceptable salt thereof, and a pharmaceutically acceptable carrier.

Embodiment I-30. A pharmaceutical composition of Embodiment I-25, wherein the pharmaceutical composition comprises at least two crystalline forms selected from
Compound 1 Form A, or a pharmaceutically acceptable salt thereof,
Compound 1 Form B, or a pharmaceutically acceptable salt thereof,
Compound 1 Form C, or a pharmaceutically acceptable salt thereof, and
Compound 1 Form D, or a pharmaceutically acceptable salt thereof,
and a pharmaceutically acceptable carrier.

Embodiment I-31. A pharmaceutical composition of Embodiment I-25, wherein the pharmaceutical composition comprises Compound 1 Form D, or a pharmaceutically acceptable salt thereof, and Compound 1 Form A, or a pharmaceutically acceptable salt thereof, and a pharmaceutically acceptable carrier.

Embodiment I-32. A pharmaceutical composition of Embodiment I-25, wherein the pharmaceutical composition comprises Compound 1 Form D, or a pharmaceutically acceptable salt thereof, and Compound 1 Form B, or a pharmaceutically acceptable salt thereof, and a pharmaceutically acceptable carrier.

Embodiment I-33. A pharmaceutical composition of Embodiment I-25, wherein the pharmaceutical composition comprises Compound 1 Form D, or a pharmaceutically acceptable salt thereof, and Compound 1 Form C, or a pharmaceutically acceptable salt thereof, and a pharmaceutically acceptable carrier.

Embodiment I-34. A method of treating a disease associated with SHP2 modulation in a subject in need thereof, comprising administering to the subject an effective amount the crystalline form of any one of Embodiments I-1 to I-24, or a pharmaceutically acceptable salt thereof.

Embodiment I-35. The method of Embodiment I-34, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment I-36. A crystalline form of any one of Embodiments I-1 to I-24, or a pharmaceutically acceptable salt thereof, for use as a medicament.

Embodiment I-37. A crystalline form of any one of Embodiments I-1 to I-24, or a pharmaceutically acceptable salt thereof, for use in treating or preventing a disease associated with SHP2 modulation.

Embodiment I-38. Use of a crystalline form of any one of Embodiment I-1 to I-24, or a pharmaceutically acceptable salt thereof, in the manufacture of a medicament for treating or preventing a disease associated with SHP2 modulation.

Embodiment I-39. A method of treating a disease associated with SHP2 modulation in a subject in need thereof, comprising administering to the subject an effective amount of a pharmaceutical composition of any one of Embodiments I-25 to I-33.

Embodiment I-40. The method of Embodiment I-39, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment I-41. A pharmaceutical composition of any one of Embodiments I-25 to I-33 for use as a medicament.

Embodiment I-42. A pharmaceutical composition of any one of Embodiments I-25 to I-33 for use in treating or preventing a disease associated with SHP2 modulation.

Embodiment I-43. Use of a pharmaceutical composition of any one of Embodiments I-25 to I-33 in the manufacture of a medicament for treating or preventing a disease associated with SHP2 modulation.

Examples

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Differential Scanning Calorimetry

Differential scanning calorimetry performed using TA Instruments Q2000: Temperature calibration was performed using NIST-traceable indium metal. The sample was placed into an aluminum Tzero crimped pan and the weight was accurately recorded. A weighed aluminum pan configured as the sample pan was placed on the reference side of the cell. The samples were analyzed from −30 to 250° C. at a ramp rate of 10° C./min.

Differential scanning calorimetry performed using Mettler-Toledo DSC3+: Temperature calibration was performed using adamantane, phenyl salicylate, indium, tin, and zinc. The sample was placed into a hermetically sealed or an open aluminum DSC pan, and the weight was accurately recorded. A weighed aluminum pan configured as the sample pan was placed on the reference side of the cell. The samples were analyzed from −30 to 250° C. at a ramp rate of 10° C./min. Although thermograms are plotted by reference temperature (x-axis), results are reported according to sample temperatures.

Infrared Spectroscopy

Infrared spectra were acquired on a Nexus 670©Fourier transform infrared (FT-IR) spectrophotometer (Thermo Nicolet) equipped with an Ever-Glo mid/far IR source, a potassium bromide (KBr) beamsplitter, and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 4 $cm^{-1}$. A background data set was acquired with a clean Ge crystal. A Log 1/R (R=reflectance) spectrum was obtained by taking a ratio of these two data sets against each other.

IR peak position variabilities are given to within 4 $cm^{-1}$, based on the observed sharpness of the peaks picked and acquisition of data using a 2 cm-1 data point spacing (4 cm-1 resolution). The peak picking was performed using OMNIC software, versions 7.2, Thermo Electron Corporation. Observed Peaks include all IR peaks for a given form, with the exclusion of very weak intensity peaks and broad peaks with poorly defined maxima.

Single Crystal Data Collection

Standard uncertainty is written in crystallographic parenthesis notation, e.g. 0.123(4) is equivalent to 0.123±0.004. A calculated XRPD pattern was generated for Cu radiation using MERCURY and the atomic coordinates, space group, and unit cell parameters from the single crystal structure. The atomic displacement ellipsoid diagram was prepared using MERCURY. Atoms are represented by 50% probability anisotropic thermal ellipsoids.

X-ray Powder Diffraction

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-m-thick films and analyzed in transmission geometry. A beam-stop, short antiscatter extension, antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror.

The data presented herein contain X-ray diffraction patterns with tables with peak lists. Accurate peak positions are listed in the tables. Under most circumstances, peaks within the range of up to about 30 (2θ) were selected. Rounding algorithms were used to round each peak to the nearest 0.010 (2θ). The location of the peaks along the horizontal axis, ° (2θ), in both the figures and the tables were automatically determined using proprietary software and rounded to two significant figures after the decimal point. Peak position variabilities are taken as 0.2° (2θ) based upon recommendations outlined in the USP discussion of variability in X-ray powder diffraction. The accuracy and precision associated with any particular measurement reported herein has not been determined. Moreover, third party measurements on independently prepared samples on different instruments may lead to variability greater than 0.2° (2θ). To calculate d-spacings, the wavelength used was 1.541874 Å, a weighted average of the Cu K$\alpha_1$ and Cu K$\alpha_2$ wavelengths. Variability associated with d-spacing estimates was calculated from the USP recommendation, at each d-spacing, and provided in the respective data tables.

Per USP guidelines, variable hydrates and solvates may display peak variances greater than 0.2° (2θ) and therefore peak variances of 0.2° (2θ) are not applicable to these materials.

For samples with only one XRPD pattern and no other means to evaluate whether the sample provides a good approximation of the powder average, peak tables contain data identified only as "Prominent Peaks". These peaks are a subset of the entire observed peak list. Prominent peaks are selected from observed peaks by identifying preferably non-overlapping, low-angle peaks, with strong intensity.

If multiple diffraction patterns are available, then assessment of particle statistics (PS) and/or preferred orientation (PO) is possible. Reproducibility among XRPD patterns from multiple samples analyzed on a single diffractometer indicates that the particle statistics are adequate. Consistency of relative intensities among XRPD patterns from different diffractometer geometries (i.e. reflection vs. transmission) indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks". In general, the more data collected to determine Representative Peaks, the more confident one can be of the classification of those peaks.

"Characteristic peaks", to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within 0.2° (2θ). Not all crystalline polymorphs of a compound necessarily have at least one characteristic peak.

Example 1—Form A

Compound 1 Form A was generated through spontaneous polymorphic conversion from either Forms C or D (or mixtures thereof) when exposed to temperatures above 80° C. Compound 1 Form A was generated from Form B (or mixtures of Form B with Forms C and/or D) when exposed to temperatures above the melt of Form B (~188° C.) but below the melt of Form A (~213° C.) and allowed to spontaneously crystallize.

A slurry of Compound 1 in methanol was stirred at ~58° C. for ~9 days. Compound 1 Form A was recovered from the slurry by water aspirator vacuum filtration.

Figure 1B:
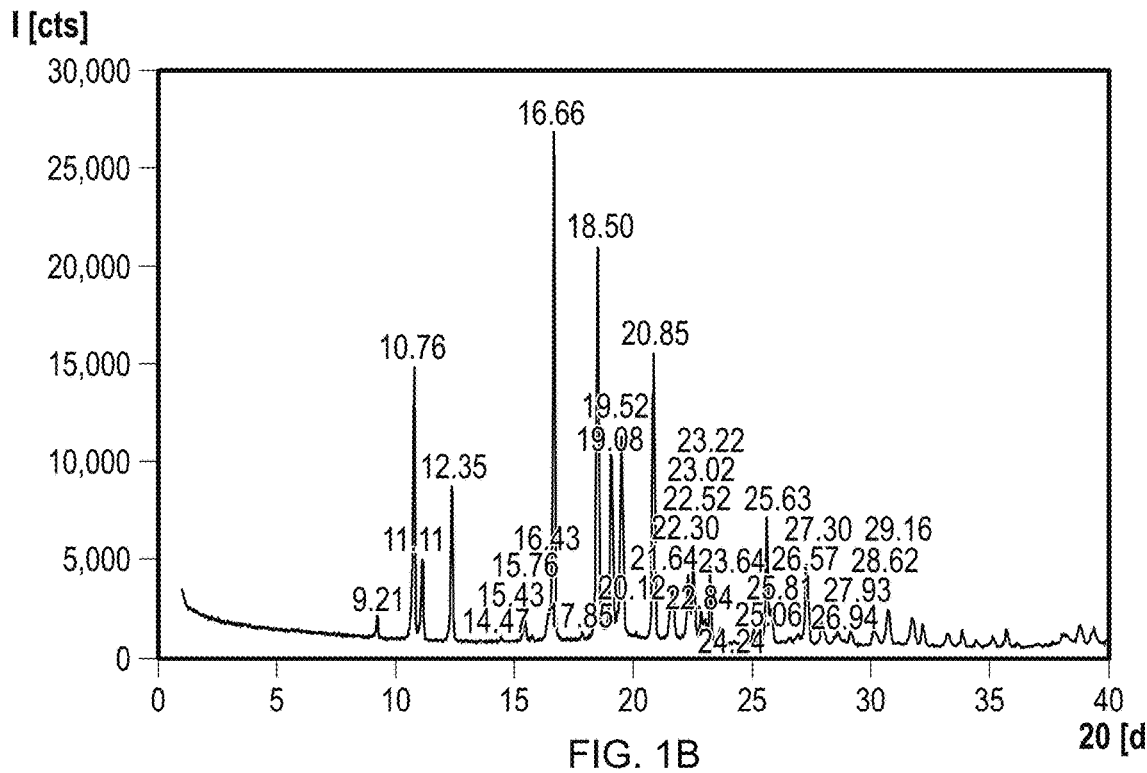
FIG. 1B is an X-ray diffraction pattern of Compound 1 Form A with observed peaks.

Compound 1 Form A was characterized by X-ray powder diffraction (XRPD), as described herein. The X-ray powder diffractogram of Compound 1 Form A is shown in FIG. 1A and FIG. 1B and the peaks and their relative intensities in the XRPD pattern are shown in Table 3.

Example 2—Form B

Preparation A: A solution of Compound 1 in dichloromethane or methanol was generated at ambient temperature and filtered with a 0.2-μm nylon filter. The filtrates were left to evaporate under ambient conditions to provide Compound 1 Form B.

Preparation B: A solution of Compound 1 in methanol was generated at approximately 50° C., treated with activated charcoal, and filtered. The filtrate was slowly cooled to ambient temperature to provide crystals of Compound 1 Form B.

The quality of the structure obtained is high, as indicated by the fit residual, R, of 0.0437 (4.37%). R-factors in the range 2%-6% are quoted to be the most reliably determined structures.

Data Collection

A colorless plate having approximate dimensions of 0.13× 0.08×0.03 mm$^3$, was mounted on a polymer loop in random orientation. Preliminary examination and data collection were performed on a Rigaku SuperNova diffractometer, equipped with a copper anode microfocus sealed X-ray tube (Cu Kα κ=1.54184 Å) and a Dectris Pilatus3 R 200K hybrid pixel array detector.

Cell constants and an orientation matrix for data collection were obtained from least-squares refinement using the setting angles of 8262 reflections in the range 3.9000°<θ<75.6370°. The space group was determined by the program CRYSALISPRO to be P1 (international tables no. 1).

The data were collected to a maximum diffraction angle (2θ) of 155.036° at room temperature.

Table 13 below shows crystal data and data collection parameters for Compound 1 Form B.

TABLE 13

| | |
|---|---|
| Empirical formula | $C_{20}H_{27}ClN_6O_2S$ |
| Formula weight (g mol$^{-1}$) | 450.98 |
| Temperature (K) | 293(2) |
| Wavelength (Å) | 1.54184 |
| Crystal system | triclinic |
| Space group | P1 |
| Unit cell parameters | |
| a = 9.65334(16) Å | α = 76.0621(15)° |
| b = 10.28825(18) Å | β = 89.6714(13)° |
| c = 11.62614(19) Å | γ = 76.4043(15)° |
| Unit cell volume (Å$^3$) | 1087.68(3) |
| Cell formula units, Z | 2 |
| Calculated density (g cm$^{-3}$) | 1.377 |
| Absorption coefficient (mm$^{-1}$) | 2.698 |
| F(000) | 476 |
| Crystal size (mm$^3$) | 0.13 × 0.08 × 0.03 |
| Reflections used for cell measurement | 8262 |
| θ range for cell measurement | 3.9000°-75.6370° |
| Total reflections collected | 19826 |
| Index ranges | −12 ≤ h ≤ 12; −12 ≤ k ≤ 12; −14 ≤ l ≤ 14 |
| θ range for data collection | $\theta_{min}$ = 3.923°, $\theta_{max}$ = 77.518° |
| Completeness to $\theta_{max}$ | 98.1% |
| Completeness to $\theta_{full}$ = 67.684° | 99.8% |

TABLE 13-continued

| | |
|---|---|
| Absorption correction | multi-scan |
| Transmission coefficient range | 0.906-1.000 |
| Refinement method | full matrix least-squares on $F^2$ |
| Independent reflections | 7360 [$R_{int}$ = 0.0355, $R_\sigma$ = 0.0400] |
| Reflections [I > 2σ(I)] | 6171 |
| Reflections/restraints/parameters | 7360/3/569 |
| Goodness-of-fit on $F^2$ | S = 1.07 |
| Final residuals [I > 2σ(I)] | R = 0.0437, $R_w$ = 0.1215 |
| Final residuals [all reflections] | R = 0.0529, $R_w$ = 0.1279 |
| Largest diff. peak and hole (e Å$^{-3}$) | 0.433, -0.255 |
| Max/mean shift/standard uncertainty | 0.000/0.000 |
| Absolute structure determination | Flack parameter: 0.011(14) |

Data Reduction

Frames were integrated with CRYSALISPRO. A total of 19826 reflections were collected, of which 7360 were unique. Lorentz and polarization corrections were applied to the data. The linear absorption coefficient is 2.698 mm-1 for Cu Kα radiation. An empirical absorption correction using CRYSALISPRO was applied. Transmission coefficients ranged from 0.906 to 1.000. Intensities of equivalent reflections were averaged. The agreement factor for the averaging was 3.55% based on intensity.

Structure Solution and Refinement

The structure was solved by charge flipping using OLEX2. The remaining atoms were located in succeeding difference Fourier syntheses. The structure was refined using SHELXL-2014. The hydroxyl and aminopyridine hydrogen atoms were refined independently. All other hydrogen atoms were included in the refinement but restrained to ride on the atom to which they are bonded. The structure was refined in full-matrix least-squares by minimizing the function:

$$\Sigma w(|F_o|^2-|F_c|^2)^2$$

where the weight, w, is defined as $1/[\sigma^2(F_o^2)+(0.0659P)^2+(0.2167P)]$, where $P=(F_o^2+2F_c^2)/3$.

Scattering factors were taken from the "International Tables for Crystallography". Of the 7360 reflections used in the refinements, only the reflections with intensities larger than twice their uncertainty [I>2σ(I)], 6171, were used in calculating the fit residual, R. The final cycle of refinement included 569 variable parameters, 3 restraints, and converged with respective unweighted and weighted agreement factors of:

$$R=\Sigma|F_o-F_c|/\Sigma F_o=0.0437$$

$$R_w=\sqrt{(\Sigma w(F_o^2-F_c^2)^2/\Sigma w(F_o^2)^2)}=0.1215$$

The standard deviation of an observation of unit weight (goodness of fit) was 1.07. The highest peak in the final difference Fourier had an electron density of 0.433 e/Å$^3$. The minimum negative peak had a value of -0.255 e/Å$^3$.

Compound 1 Form B was characterized by X-ray powder diffraction (XRPD), as described herein. The X-ray powder diffractogram of Compound 1 Form B is shown in FIG. 3A, FIG. 3B, FIG. 3C, and FIG. 3D and the peaks and their relative intensities in the XRPD pattern are shown in Table 6.

Example 3—Form C

In general, Compound 1 Form C is generated through spontaneous polymorphic conversion from either Compound 1 Forms D or A (or mixtures thereof) when exposed to temperatures between approximately 43 and 80° C.

A slurry of Compound 1 in methanol was heated to reflux and filtered by water aspirator vacuum filtration. The filtrate was returned to boil, treated with activated charcoal, and filtered again by water aspirator vacuum filtration. The filtrate was rotary evaporated to dryness, briefly triturated in diethyl ether, filtered by water aspirator vacuum filtration, and dried under nitrogen. The solids were used to generate a slurry in methanol and stirred at −58° C. for ~6 days to provide crystals of Compound 1 Form C.

The quality of the structure obtained is high, as indicated by the fit residual, R, of 0.0523 (5.23%). R-factors in the range 2%-6% are quoted to be the most reliably determined structures.

Data Collection

A colorless plate having approximate dimensions of 0.11× 0.08×0.02 mm$^3$, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector.

Cell constants and an orientation matrix for data collection were obtained from least-squares refinement using the setting angles of 9466 reflections in the range 3.6150°<θ<76.7550. The space group was determined by the program CRYSALISPRO to be $P2_12_12$ (international tables no. 18).

The data were collected to a maximum diffraction angle (2θ) of 155.666° at room temperature.

Table 14 below shows crystal data and data collection parameters for Compound 1 Form C.

TABLE 14

| | |
|---|---|
| Empirical formula | $C_{20}H_{27}ClN_6O_2S$ |
| Formula weight (g mol$^{-1}$) | 450.98 |
| Temperature (K) | 300.7(5) |
| Wavelength (Å) | 1.54184 |
| Crystal system | orthorhombic |
| Space group | $P2_12_12$ |
| Unit cell parameters | |
| a = 47.6458(8) Å | α = 90° |
| b = 14.4005(2) Å | β = 90° |
| c = 9.5460(2) Å | γ = 90° |
| Unit cell volume (Å$^3$) | 6549.8(2) |
| Cell formula units, Z | 12 |
| Calculated density (g cm$^{-3}$) | 1.372 |
| Absorption coefficient (mm$^{-1}$) | 2.688 |
| F(000) | 2856 |
| Crystal size (mm$^3$) | 0.11 × 0.08 × 0.02 |
| Reflections used for cell measurement | 9466 |
| θ range for cell measurement | 3.6150°-76.7550° |
| Total reflections collected | 35304 |
| Index ranges | −47 ≤ h ≤ 59; −18 ≤ k ≤ 17; −11 ≤ l ≤12 |
| θ range for data collection | $θ_{min}$ = 3.206°, $θ_{max}$ = 77.833° |
| Completeness to $θ_{max}$ | 98% |
| Completeness to $θ_{full}$ = 67.684° | 99.9% |
| Absorption correction | multi-scan |
| Transmission coefficient range | 0.848-1.000 |
| Refinement method | full matrix least-squares on $F^2$ |
| Independent reflections | 13544 [$R_{int}$ = 0.0425, $R_\sigma$ = 0.0534] |
| Reflections [I > 2σ(I)] | 9187 |
| Reflections/restraints/parameters | 13544/0/860 |
| Goodness-of-fit on $F^2$ | S = 1.01 |
| Final residuals [I > 2σ(I)] | R = 0.0523, $R_w$ = 0.1232 |
| Final residuals [all reflections] | R = 0.0854, $R_w$ = 0.1425 |
| Largest diff. peak and hole (e Å$^{-3}$) | 0.364, -0.207 |
| Max/mean shift/standard uncertainty | 0.001/0.000 |
| Absolute structure determination | Flack parameter: −0.005(9) |

Data Reduction

Frames were integrated with CrysAlisPro. A total of 35304 reflections were collected, of which 13544 were unique. Lorentz and polarization corrections were applied to the data. The linear absorption coefficient is 2.688 mm$^{-1}$ for Cu K$\alpha$ radiation. An empirical absorption correction using CrysAlisPro was applied. Transmission coefficients ranged from 0.848 to 1.000. Intensities of equivalent reflections were averaged. The agreement factor for the averaging was 4.25% based on intensity.

Structure Solution and Refinement

The structure was solved by direct methods using SHELXT. The remaining atoms were located in succeeding difference Fourier syntheses. The structure was refined using SHELXL-2014. Hydrogen atoms residing on the aminopyridine —NH$_2$ moiety were refined independently. All other hydrogen atoms were included in the refinement but restrained to ride on the atom to which they are bonded. The structure was refined in full-matrix least-squares by minimizing the function:

$$\Sigma w(|F_o|^2-|F_c|^2)^2$$

where the weight, w, is defined as $1/[\sigma^2(F_o^2)+(0.0681P)^2+(0.8040P)]$, where $P=(F_o^2+2F_c^2)/3$.

Scattering factors were taken from the "International Tables for Crystallography". Of the 13544 reflections used in the refinements, only the reflections with intensities larger than twice their uncertainty [I>2(1)], 9187, were used in calculating the fit residual, R. The final cycle of refinement included 860 variable parameters, 0 restraints, and converged with respective unweighted and weighted agreement factors of:

$$R=\Sigma|F_o-F_c|/\Sigma F_o=0.0523$$

$$R_w=\sqrt{(\Sigma w(F_o^2-F_c^2)^2/\Sigma w(F_o^2)^2)}=0.1232$$

The standard deviation of an observation of unit weight (goodness of fit) was 1.01. The highest peak in the final difference Fourier had an electron density of 0.364 e/Å$^3$. The minimum negative peak had a value of −0.207 e/Å$^3$.

Figure 8A:
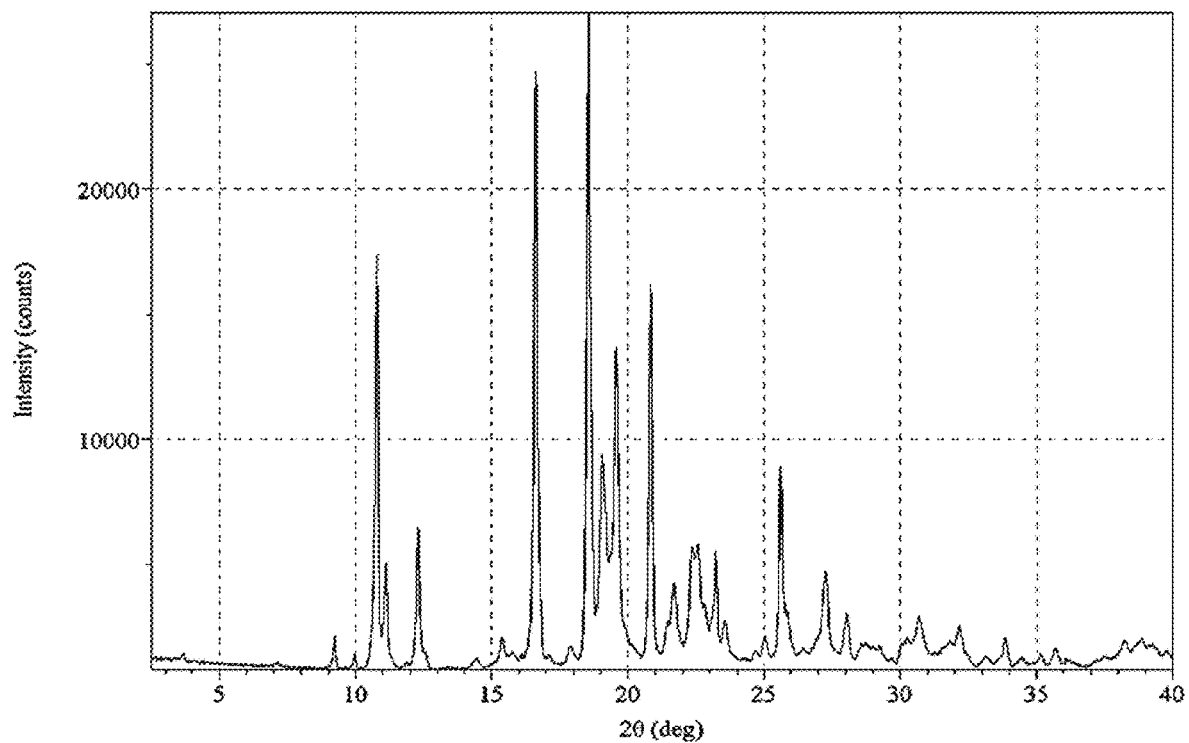
FIG. 8A is an X-ray diffraction pattern of Compound 1 Form C.
Figure 8B:
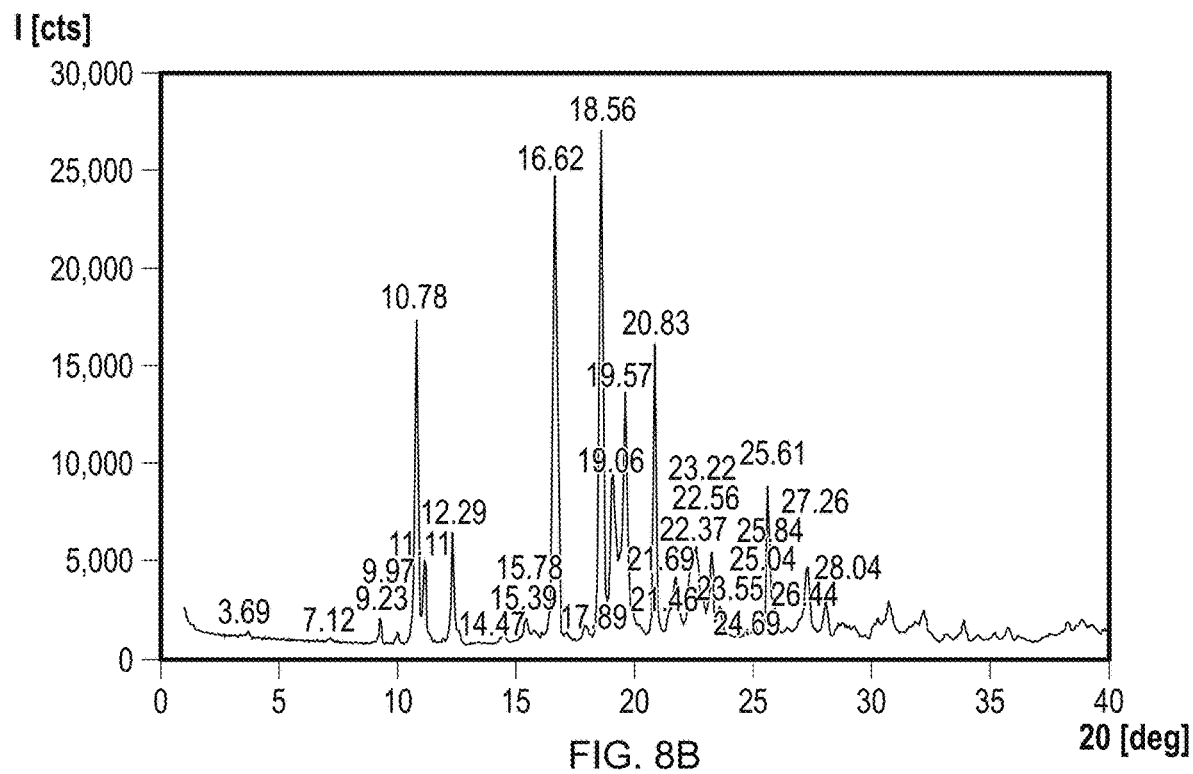
FIG. 8B is an X-ray diffraction pattern of Compound 1 Form C with observed peaks.

Compound 1 Form C was characterized by X-ray powder diffraction (XRPD), as described herein. The X-ray powder diffractogram of Compound 1 Form C is shown in FIG. 8A and FIG. 8B and the peaks and their relative intensities in the XRPD pattern are shown in Table 8.

Example 4—Form D

Preparation A: A slurry of Compound 1 in methanol was heated to reflux and filtered by water aspirator vacuum filtration. The filtrate was treated with activated charcoal and filtered again by water aspirator vacuum filtration. The activated charcoal treatment with filtration was repeated three times. The volume of the filtrate was reduced to less than a quarter of the original volume under a purge of nitrogen, providing solids. The solids were harvested by water aspirator vacuum filtration and washed with methanol. A slurry of the solids in methanol was stirred at ambient temperature for ~14 days. Compound 1 Form D was recovered from the slurry by water aspirator vacuum filtration.

Preparation B: A slurry of Compound 1 in methanol was heated to reflux and filtered by water aspirator vacuum filtration. The filtrate was returned to boil, treated with activated charcoal, and filtered again by water aspirator vacuum filtration. The filtrate was rotary evaporated to dryness, briefly triturated in diethyl ether, filtered by water aspirator vacuum filtration, and dried under nitrogen. Particles from the resulting solids were heated in mineral oil until crystals in the shape of geometric plates formed. The crystals were left in the mineral oil for ~1 month at ambient temperature and allowed to convert to Compound 1 Form D before isolating.

The quality of the structure obtained is high, as indicated by the fit residual, R, of 0.0411 (4.11%). R-factors in the range 2%-6% are quoted to be the most reliably determined structures.

Data Collection

A colorless plate having approximate dimensions of 0.19× 0.08×0.02 mm$^3$, was mounted on a polymer loop in random orientation. Preliminary examination and data collection were performed on a Rigaku SuperNova diffractometer, equipped with a copper anode microfocus sealed X-ray tube (Cu K$\alpha$ $\lambda$=1.54184 Å) and a Dectris Pilatus3 R 200K hybrid pixel array detector.

Cell constants and an orientation matrix for data collection were obtained from least-squares refinement using the setting angles of 7387 reflections in the range 3.6090°<<75.8260°. The space group was determined by the program CrysAlisPro to be P2$_1$2$_1$2$_1$ (international tables no. 19).

The data were collected to a maximum diffraction angle (2θ) of 155.176° at room temperature.

Data Reduction

Frames were integrated with CrysAlisPro. A total of 22901 reflections were collected, of which 8903 were unique. Lorentz and polarization corrections were applied to the data. The linear absorption coefficient is 2.717 mm-1 for Cu K$\alpha$ radiation. An empirical absorption correction using CrysAlisPro was applied. Transmission coefficients ranged from 0.888 to 1.000. Intensities of equivalent reflections were averaged. The agreement factor for the averaging was 3.54% based on intensity.

Structure Solution and Refinement

The structure was solved by direct methods using SHELXT. The remaining atoms were located in succeeding difference Fourier syntheses. The structure was refined using SHELXL-2014. Hydrogen atoms residing on carbon and one hydroxyl were included in the refinement but restrained to ride on the atom to which they are bonded. All other non-carbon hydrogen atoms were refined independently. The structure was refined in full-matrix least-squares by minimizing the function:

$$\Sigma w(|F_o|^2-|F_c|^2)^2$$

where the weight, w, is defined as $1/[\sigma^2(F_o^2)+(0.0510P)^2+(0.2939P)]$, where $P=(F_o^2+2F_c^2)/3$.

Scattering factors were taken from the "International Tables for Crystallography". Of the 8903 reflections used in the refinements, only the reflections with intensities larger than twice their uncertainty [I>2σ(I)], 6898, were used in calculating the fit residual, R. The final cycle of refinement included 582 variable parameters, 0 restraints, and converged with respective unweighted and weighted agreement factors of:

$$R=\sum|F_o-F_c|/\sum F_o = 0.0411$$

$$R_w = \sqrt{(\sum w(F_o^2-F_c^2)^2/\sum w(F_o^2)^2)} = 0.0970$$

The standard deviation of an observation of unit weight (goodness of fit) was 1.02. The highest peak in the final difference Fourier had an electron density of 0.224 e/Å$^3$. The minimum negative peak had a value of −0.207 e/Å$^3$.

Figure 10A:
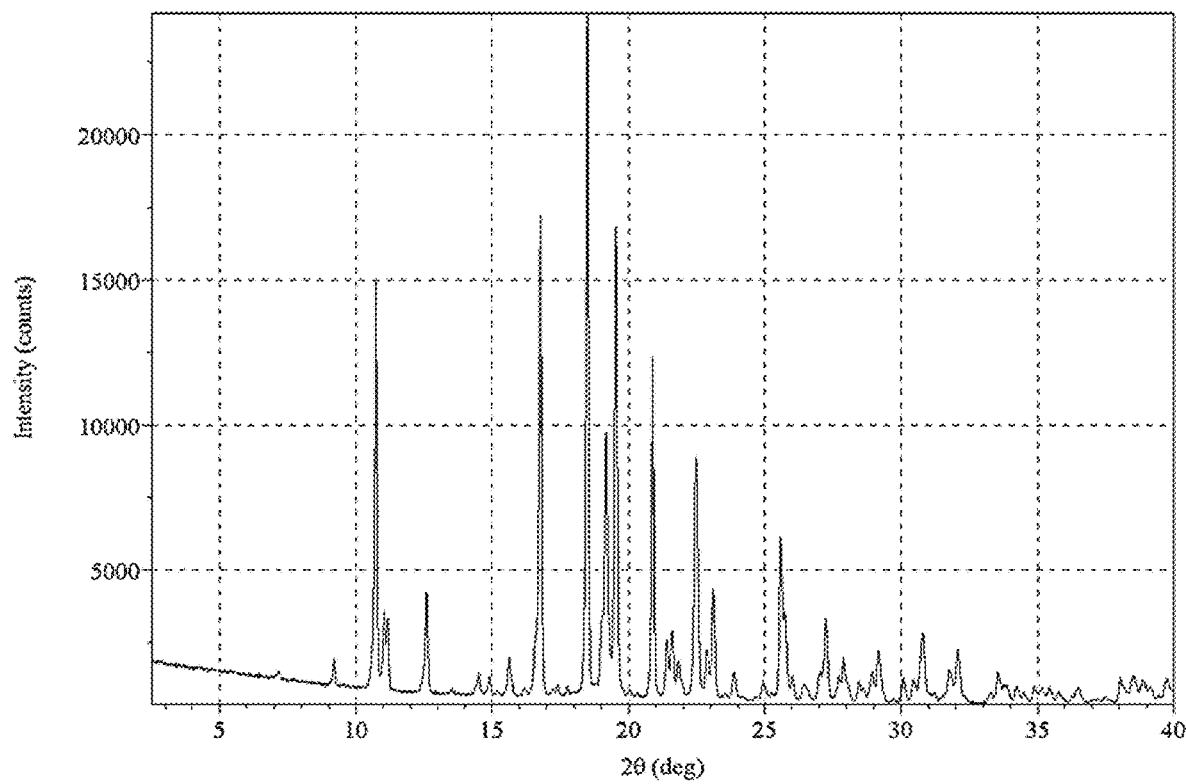
FIG. 10A is an X-ray diffraction pattern of Compound 1 Form D.
Figure 10B:
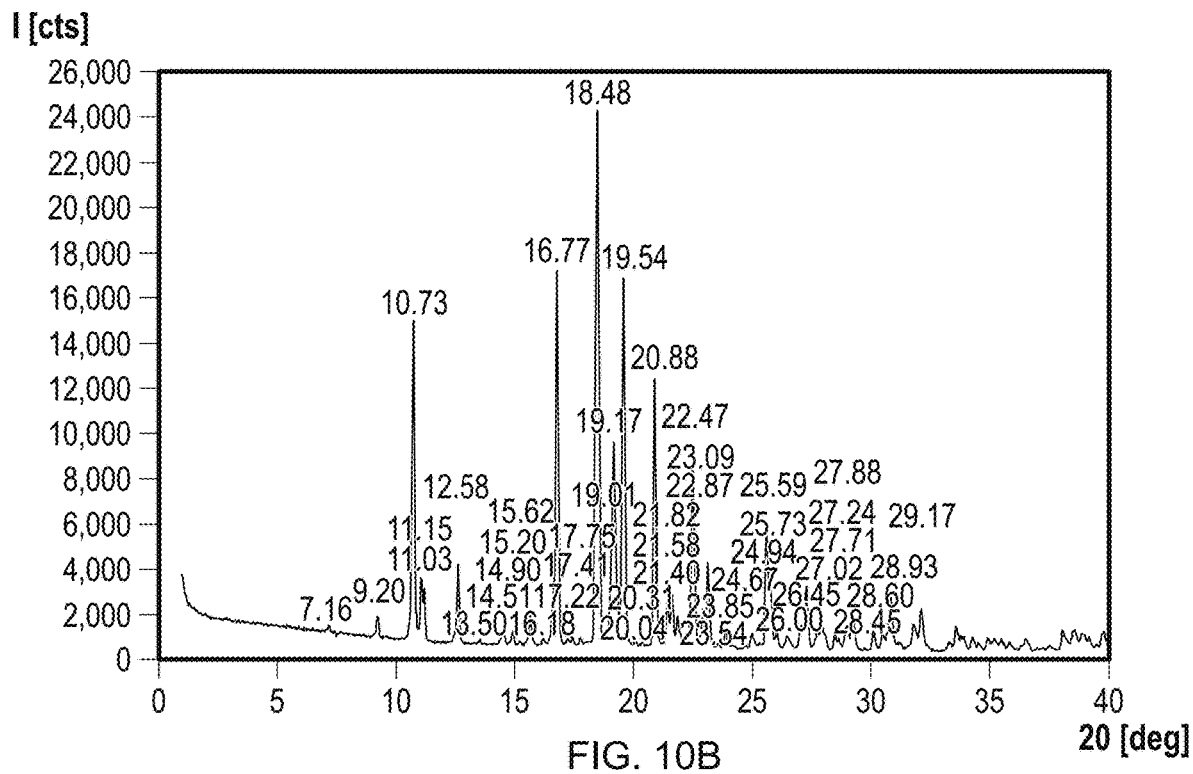
FIG. 10B is an X-ray diffraction pattern of Compound 1 Form D with observed peaks.

Compound 1 Form D was characterized by X-ray powder diffraction (XRPD), as described herein. The X-ray powder diffractogram of Compound 1 Form D is shown in FIG. 10A and FIG. 10B and the peaks and their relative intensities in the XRPD pattern are shown in Table 11.

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

What is claimed is:

1. A crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form D.

2. The crystalline form of claim 1, wherein the crystalline form is {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol.

3. The crystalline form of claim 1, or a pharmaceutically acceptable salt thereof, wherein an X-ray powder diffraction pattern comprises 2θ values: about 18.48 and about 16.77.

4. The crystalline form of claim 2, or a pharmaceutically acceptable salt thereof, wherein the X-ray powder diffraction pattern further comprises one or more 2θ values selected from the group consisting of about 10.73, about 11.03, about 11.15, about 12.58, about 19.17, about 19.54, about 20.88, about 22.47, and about 25.59.

5. The crystalline form of claim 1, or a pharmaceutically acceptable salt thereof, wherein the X-ray powder diffraction pattern is substantially in accordance with that shown in FIG. 10A.

6. The crystalline form of claim 1, or a pharmaceutically acceptable salt thereof, wherein a differential scanning calorimetry (DSC) curve comprises an endotherm at about 51° C., about 90° C., or about 211° C.

7. The crystalline form of claim 1, or a pharmaceutically acceptable salt thereof, wherein the DSC curve is substantially as shown in FIG. 13.

8. A crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form B.

9. The crystalline form of claim 8, or a pharmaceutically acceptable salt thereof, wherein an X-ray powder diffraction pattern comprises 2θ values: about 20.0 and about 17.9.

10. The crystalline form of claim 9, or a pharmaceutically acceptable salt thereof, wherein the X-ray powder diffraction pattern further comprises one or more 2θ values selected from the group consisting of about 7.8, about 9.1, about 9.4, about 11.4, about 12.8, about 13.4, about 15.7, about 18.9, about 20.9, about 23.1, and about 25.0.

11. The crystalline form of claim 8, or a pharmaceutically acceptable salt thereof, wherein the X-ray powder diffraction pattern is substantially in accordance with that shown in FIG. 3A.

12. The crystalline form of claim 8, or a pharmaceutically acceptable salt thereof, wherein the DSC curve is substantially as shown in FIG. 6.

13. A crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form C.

14. The crystalline form of claim 13, or a pharmaceutically acceptable salt thereof, wherein an X-ray powder diffraction pattern comprises 2θ values: about 18.56 and about 16.62.

15. The crystalline form of claim 14, or a pharmaceutically acceptable salt thereof, wherein the X-ray powder diffraction pattern further comprises one or more 2θ values selected from the group consisting of about 10.78, about 11.11, about 12.29, about 19.06, about 19.57, about 20.83, and about 25.61.

16. The crystalline form of claim 13, or a pharmaceutically acceptable salt thereof, wherein the X-ray powder diffraction pattern is substantially in accordance with that shown in FIG. 8A.

17. A crystalline form of {6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol, or a pharmaceutically acceptable salt thereof, characterized as Compound 1 Form A.

18. The crystalline form of claim 17, or a pharmaceutically acceptable salt thereof, wherein an X-ray powder diffraction pattern comprises 2θ values: about 16.66 and about 18.50.

19. The crystalline form of claim 18, or a pharmaceutically acceptable salt thereof, wherein the X-ray powder diffraction pattern further comprises one or more 2θ values selected from the group consisting of about 10.76, about 11.11, about 12.35, about 19.08, about 19.52, about 20.85, and about 25.63.

20. The crystalline form of claim 17, or a pharmaceutically acceptable salt thereof, wherein the X-ray powder diffraction pattern is substantially in accordance with that shown in FIG. 1A.

21. A pharmaceutical composition comprising the crystalline form of claim 1, or a pharmaceutically acceptable salt thereof, and a pharmaceutically acceptable carrier.

22. A pharmaceutical composition comprising the crystalline form of claim 8, or a pharmaceutically acceptable salt thereof, and a pharmaceutically acceptable carrier.

23. A pharmaceutical composition comprising the crystalline form of claim 13, or a pharmaceutically acceptable salt thereof, and a pharmaceutically acceptable carrier.

24. A pharmaceutical composition comprising a crystalline form of claim 17, or a pharmaceutically acceptable salt thereof, and a pharmaceutically acceptable carrier.

25. A pharmaceutical composition of claim 21, wherein the pharmaceutical composition further comprises one or more crystalline forms selected from the group consisting of Compound 1 Form A, or a pharmaceutically acceptable salt thereof, Compound 1 Form B, or a pharmaceutically acceptable salt thereof, and Compound 1 Form C, or a pharmaceutically acceptable salt thereof;

and a pharmaceutically acceptable carrier.

26. A method of treating a disease associated with SHP2 modulation in a subject in need thereof, comprising administering to the subject an effective amount of the crystalline form of claim 1, or a pharmaceutically acceptable salt thereof, wherein the disease is selected from Noonan Syndrome, Leopard Syndrome, juvenile myelomonocytic leukemias, neuroblastoma, melanoma, acute myeloid leukemia and cancers of the breast, lung and colon.

27. A method of treating a disease associated with SHP2 modulation in a subject in need thereof, comprising administering to the subject an effective amount of the crystalline form of claim 8, or a pharmaceutically acceptable salt thereof, wherein the disease is selected from Noonan Syndrome, Leopard Syndrome, juvenile myelomonocytic leukemias, neuroblastoma, melanoma, acute myeloid leukemia and cancers of the breast, lung and colon.

28. A method of treating a disease associated with SHP2 modulation in a subject in need thereof, comprising administering to the subject an effective amount of the crystalline form of claim 13, or a pharmaceutically acceptable salt thereof, wherein the disease is selected from Noonan Syndrome, Leopard Syndrome, juvenile myelomonocytic leukemias, neuroblastoma, melanoma, acute myeloid leukemia and cancers of the breast, lung and colon.

29. A method of treating a disease associated with SHP2 modulation in a subject in need thereof, comprising administering to the subject an effective amount of the crystalline form of claim 17, or a pharmaceutically acceptable salt thereof, wherein the disease is selected from Noonan Syndrome, Leopard Syndrome, juvenile myelomonocytic leukemias, neuroblastoma, melanoma, acute myeloid leukemia and cancers of the breast, lung and colon.

30. A method of treating a disease associated with SHP2 modulation in a subject in need thereof, comprising administering to the subject an effective amount of the crystalline form of claim 1, or a pharmaceutically acceptable salt thereof, wherein the disease is selected from esophageal cancer, gastric carcinoma, anaplastic large-cell lymphoma, and glioblastoma.

31. A method of treating a disease associated with SHP2 modulation in a subject in need thereof, comprising administering to the subject an effective amount of the crystalline form of claim 8, or a pharmaceutically acceptable salt thereof, wherein the disease is selected from esophageal cancer, gastric carcinoma, anaplastic large-cell lymphoma, and glioblastoma.

32. A method of treating a disease associated with SHP2 modulation in a subject in need thereof, comprising administering to the subject an effective amount of the crystalline form of claim 13, or a pharmaceutically acceptable salt thereof, wherein the disease is selected from esophageal cancer, gastric carcinoma, anaplastic large-cell lymphoma, and glioblastoma.

33. A method of treating a disease associated with SHP2 modulation in a subject in need thereof, comprising administering to the subject an effective amount of the crystalline form of claim 17, or a pharmaceutically acceptable salt thereof, wherein the disease is selected from esophageal cancer, gastric carcinoma, anaplastic large-cell lymphoma, and glioblastoma.

* * * * *